US009913988B2

United States Patent
Yoder et al.

(10) Patent No.: US 9,913,988 B2
(45) Date of Patent: Mar. 13, 2018

(54) SYSTEMS, APPARATUS, METHODS AND COMPUTER-READABLE STORAGE MEDIA FACILITATING TELEMETRY WITH AN IMPLANTABLE DEVICE

(71) Applicant: Medtronic, Inc., Minneapolis, MN (US)

(72) Inventors: Matthew R. Yoder, Crystal, MN (US); Daniel M. Gelfman, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 13 days.

(21) Appl. No.: 14/634,093

(22) Filed: Feb. 27, 2015

(65) Prior Publication Data

US 2016/0250486 A1 Sep. 1, 2016

(51) Int. Cl.
*G08C 19/22* (2006.01)
*A61N 1/372* (2006.01)
*G06F 19/00* (2018.01)

(52) U.S. Cl.
CPC ..... *A61N 1/37217* (2013.01); *G06F 19/3406* (2013.01); *A61N 1/37252* (2013.01)

(58) Field of Classification Search
CPC .. A61N 1/37217; A61N 1/37252; H04Q 9/02; H01S 2301/04; H01S 2303/00; H01S 3/06754; H01S 3/1608; H04B 10/2912; H04B 10/2935; H04J 14/0221; G06F 19/3406
USPC .................................................... 340/870.07
See application file for complete search history.

(56) References Cited

U.S. PATENT DOCUMENTS

| 4,545,380 | A | 10/1985 | Schroeppel |
| 7,934,508 | B2 | 5/2011 | Behm |
| 8,145,320 | B2 | 3/2012 | Corndorf et al. |
| 8,700,137 | B2 | 4/2014 | Albert |
| 8,792,983 | B2 | 7/2014 | Von Arx et al. |
| 9,686,022 | B2 * | 6/2017 | Scordilis ................ H04B 17/00 |

(Continued)

OTHER PUBLICATIONS

Dirksen, J., "HTML5: Remotely vibrate a phone with morse code using web sockets and the vibrate API," Smartjava.org, May 15, 2012, 6 pages, http://www.smartjava.org/content/html5-remotely-vibrate-phone-morse-code-using-web-sockets-and-vibrate-api.

*Primary Examiner* — Ojiako Nwugo

(57) ABSTRACT

Techniques for facilitating telemetry with an implantable device are provided. In one embodiment, an implantable device includes a detection component configured to detect first vibration activity generated by a mobile electronic device external to the implantable device. The first vibration activity includes one or more defined vibration behaviors. The implantable device further includes a memory that stores executable components, and a processor that executes the executable components stored in the memory. In some embodiments, an executable component includes an analysis component configured to determine whether the first vibration activity has a defined level of similarity with a first vibration pattern identifier. Another executable component can include a communication component configured to conduct a telemetry session between the implantable device and the mobile electronic device based on a determination that the first vibration activity has the defined level of similarity with the first vibration pattern identifier.

28 Claims, 12 Drawing Sheets

(56) References Cited

U.S. PATENT DOCUMENTS

| | | | |
|---|---|---|---|
| 2005/0165321 A1* | 7/2005 | Fischell | A61B 5/0452 600/515 |
| 2006/0074455 A1* | 4/2006 | Strandberg | A61N 1/37252 607/30 |
| 2008/0077031 A1* | 3/2008 | Spinelli | A61N 1/37282 600/513 |
| 2009/0228073 A1 | 9/2009 | Scholten | |
| 2009/0270949 A1 | 10/2009 | Kalpin et al. | |
| 2011/0172743 A1* | 7/2011 | Davis | A61B 5/0031 607/62 |
| 2012/0109259 A1* | 5/2012 | Bond | A61N 1/025 607/60 |
| 2012/0197347 A1* | 8/2012 | Olson | A61N 1/37217 607/60 |
| 2013/0046354 A1* | 2/2013 | Frustaci | A61B 5/0555 607/6 |
| 2013/0289652 A1* | 10/2013 | Skelton | A61N 1/36139 607/46 |
| 2013/0293494 A1* | 11/2013 | Reshef | G06F 3/016 345/173 |
| 2014/0266933 A1* | 9/2014 | Andersen | H01Q 1/273 343/718 |
| 2015/0119846 A1* | 4/2015 | Joglekar | A61N 1/37276 604/500 |
| 2015/0148868 A1* | 5/2015 | Shahandeh | A61N 1/37276 607/60 |
| 2016/0128572 A1* | 5/2016 | van Kessel | A61B 5/0028 600/309 |

\* cited by examiner

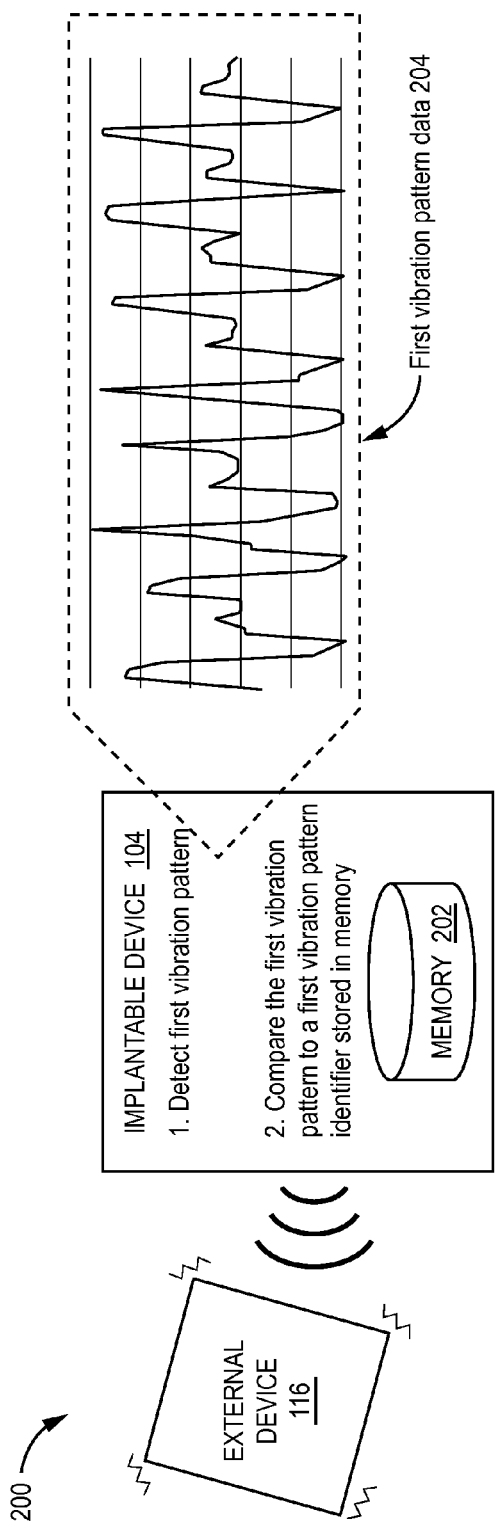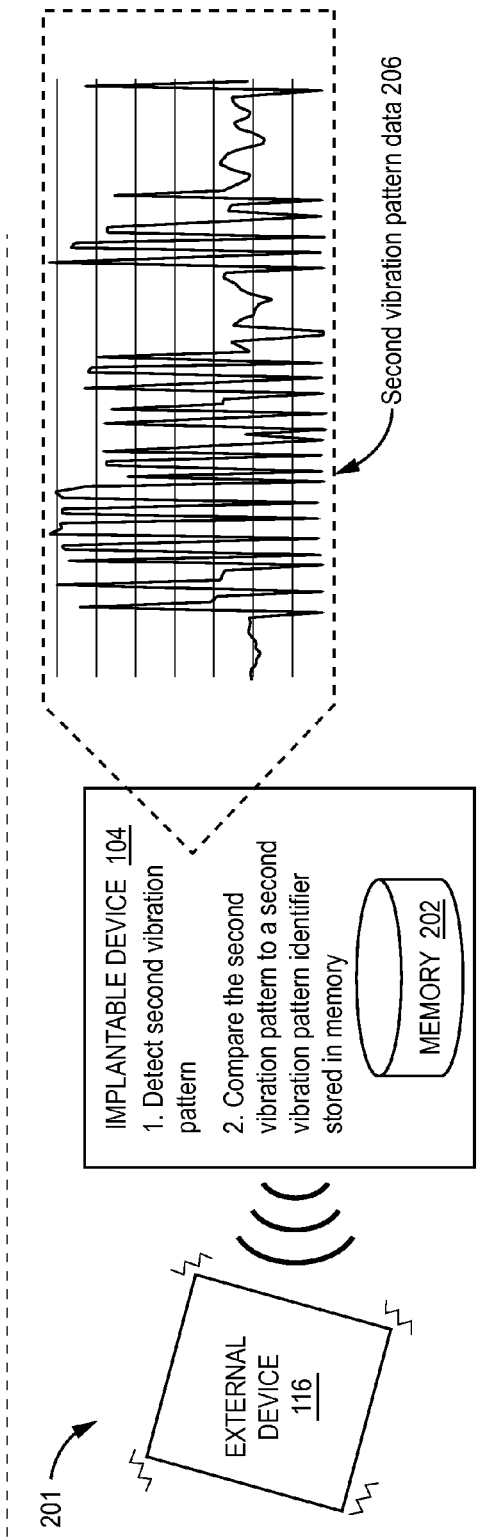
FIG. 2A
FIG. 2B

SYSTEMS, APPARATUS, METHODS AND COMPUTER-READABLE STORAGE MEDIA FACILITATING TELEMETRY WITH AN IMPLANTABLE DEVICE

TECHNICAL FIELD

This disclosure relates generally to implantable devices and, more particularly, to systems, apparatus, methods and computer-readable storage media facilitating telemetry with an implantable device.

BACKGROUND

Implantable medical devices (IMDs) monitor and treat physiological conditions within the body. These devices, including pacemakers, implantable cardiac defibrillators (ICDs), drug delivery systems, and neurostimulators, can help manage a broad range of ailments, such as cardiac arrhythmia, diabetes, and Parkinson's disease. Medical care providers can monitor the IMD and assess patient current and historical physiological state to predict impending events or conditions. Providers can also initiate and/or modify treatment plans from time to time and/or evaluate patient compliance with nutrition, exercise and general care regiments based on data recorded in the IMD. Additionally, laboratory personnel can perform IMD diagnostics to improve function efficiencies and detection of low remaining battery life.

The latest IMDs support delivery of telemetry for remote monitoring and control. The information communicated between an IMD and a remote device using telemetry is often highly sensitive and personal. However, measures for ensuring that information is communicated from the IMD in trusted scenarios are limited. Balancing security and privacy with safety and efficacy will become increasingly important as IMD technologies evolve.

Today, the proximity necessary to use the inductive telemetry protocol provides a certain amount of security and allows active IMDs to pass data and accept data from a device external to the body of the patient. Inductive telemetry uses the mutual inductance established between two closely-placed coils. This type of telemetry is referred to as inductive telemetry or near-field telemetry because the coils must typically be closely situated for obtaining inductively coupled communication. However, the ability to use inductive telemetry protocol, and especially proprietary inductive telemetry protocols, is limited to devices fitted to perform inductive technology. As such, a majority of existing personal consumer electronic devices are unable to be utilized for IMD telemetry. Accordingly, there is a business desire to use commercially available telemetry protocols in order to more easily facilitate widespread provisioning of telemetry solutions while maintaining the security safeguards associated with inductive telemetry protocols.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, apparatus, methods and computer-readable storage media facilitating telemetry with an implantable device based on vibration of an external device. In some embodiments, the implantable device is or includes an IMD. In other embodiments, the implantable device is or includes a device configured to interact with the IMD. In these embodiments, both the implantable device and the IMD can be implanted within a patient.

In an embodiment, an implantable device is provided that includes a detection component configured to detect first vibration activity generated by a mobile electronic device external to the implantable device. The first vibration activity includes one or more defined vibration behaviors. The implantable device further includes a memory that stores executable components, and a processor that executes the executable components stored in the memory. The executable components include an analysis component configured to determine whether the first vibration activity has a defined level of similarity with a first vibration pattern identifier, and a communication component configured to conduct a telemetry session between the implantable device and the mobile electronic device based on a determination that the first vibration activity has the defined level of similarity with the first vibration pattern identifier. The communication component is further configured to facilitate communication of security information between the implantable device and the mobile electronic device based on the determination that the first vibration activity has the defined level of similarity with the first vibration pattern identifier. The detection component can include one or more vibration sensors including, but not limited to, an accelerometer or a piezoelectric device.

In another embodiment, an implantable device is disclosed that includes a detection component configured to detect first vibration activity generated by an electronic device external to the implantable device. The first vibration activity includes one or more defined vibration behaviors. The implantable device further includes an analysis component configured to determine whether the first vibration activity has a defined correlation with a first vibration pattern identifier, and a communication component configured to facilitate one of a plurality of levels of communication between the electronic device and the implantable device based on a determination that the first vibration activity has the defined correlation with first vibration pattern identifier, and based on a determination of whether the first vibration activity is a first iteration of vibration activity or a second iteration of vibration activity. In accordance with this embodiment, the first iteration of vibration activity and the second iteration of vibration activity are associated with different vibration behaviors. In other embodiments, the first iteration of vibration activity and the second iteration of vibration activity are associated with the same vibration behaviors.

In another embodiment, a computer-readable storage medium is provided. The computer-readable storage medium stores executable instructions that, in response to execution, cause a device including a processor to perform operations. These operations include detecting first vibration activity generated by an electronic device external to an implantable device. The first vibration activity includes one or more defined vibration behaviors. The operations also include determining whether the first vibration activity has a defined correlation with a first vibration pattern identifier. The operations further include facilitating communication associated with one of a plurality of levels of communication between the electronic device and the implantable device based on determining that the first vibration activity has the defined correlation with the first vibration pattern identifier, and based on determining whether the first vibration activity is a first iteration of vibration activity or a second iteration of vibration activity. In some embodiments, the electronic device can be or include the external device described herein.

In yet another embodiment, a system is described. The system includes an electronic device having one or more computer-readable instructions executable to generate first vibration activity of the electronic device, and an implantable device. The first vibration activity includes one or more defined vibration behaviors. The implantable device includes a detection component configured to detect the first vibration activity generated by the electronic device based on a location of the electronic device external to and within a defined proximity of the implantable device. The implantable device also includes an analysis component configured to determine whether the first vibration activity has a defined level of similarity with a first vibration pattern identifier. The implantable device also includes a communication component configured to conduct a telemetry session between the implantable device and the electronic device based on a determination that the first vibration activity corresponds to the first vibration pattern identifier. In some embodiments, the system further includes a server device configured to transmit information to the electronic device. The information is indicative of the one or more computer-readable instructions to generate the first vibration activity of the electronic device.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

BRIEF DESCRIPTION OF THE DRAWINGS

FIGS. 2A and 2B illustrate respective block diagrams of example, non-limiting systems depicting generation and detection of vibration patterns facilitating telemetry with an implantable device based on vibration of an external device in accordance with one or more embodiments described herein.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
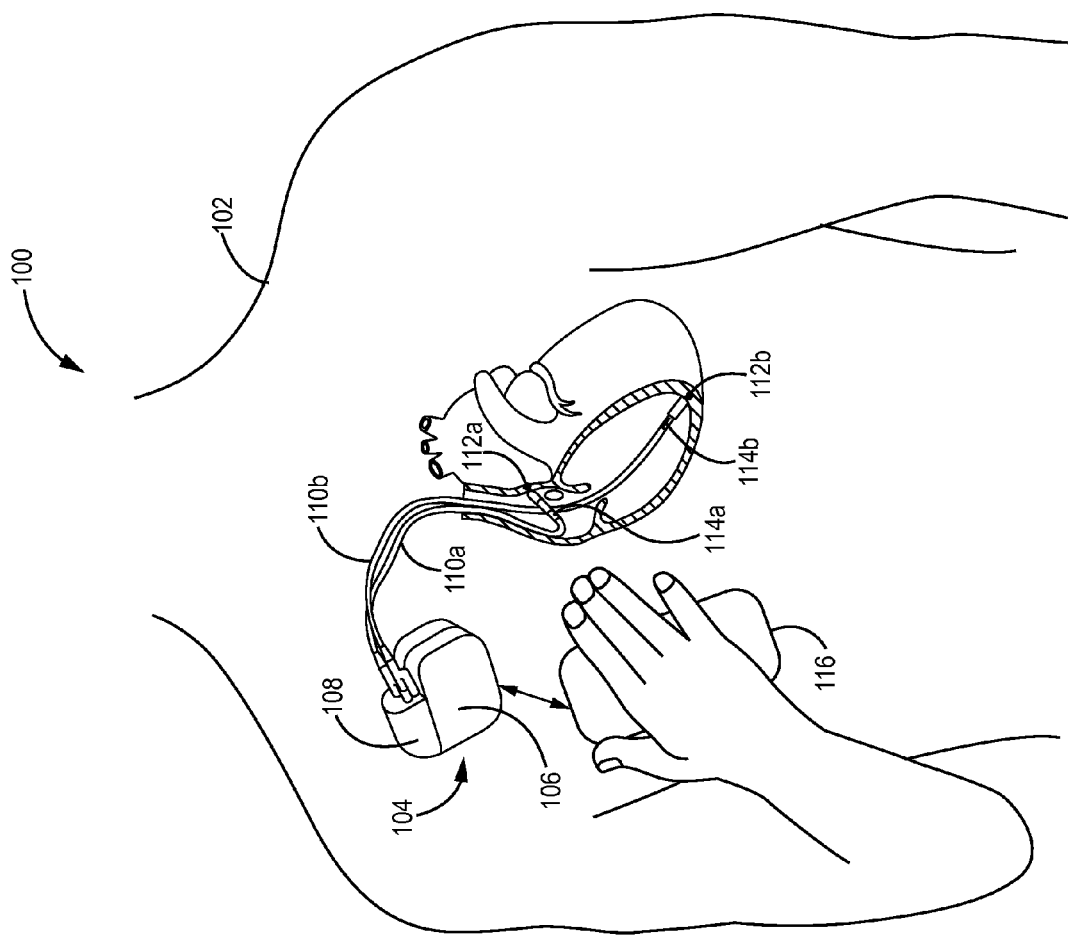
FIG. 1 illustrates an example schematic diagram of an example, non-limiting medical device telemetry system facilitating telemetry with an implantable device based on vibration of an external device in accordance with one or more embodiments described herein.

With reference now to the drawings, FIG. 1 illustrates an example schematic diagram of an exemplary, non-limiting medical device telemetry system 100 facilitating telemetry between an implantable device and an external device based on vibration of the external device in accordance with one or more embodiments described herein. In the embodiment shown, system 100 includes an implantable device 104 implanted within a body 102, and an external device 116.

Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machine to perform the operations described.

One or more embodiments of system 100 are described in connection with facilitating telemetry between the implantable device 104 and the external device 116 based on vibration of the external device 116. In one embodiment, for example, the external device 116 can be configured with hardware, software or a combination of hardware and software that can cause a vibration to be generated by the external device 116. In some embodiments, the vibration corresponds to a unique vibration pattern. For example, the external device 116 can be activated (e.g., by a patient in which the implantable device 104 is implanted, physician, nurse, or other user) to perform vibration of the external device 116 via an application of the external device 116 in conjunction with a vibrator as described in greater detail below with reference to FIG. 5. The vibration of the external device 116 can be in accordance with a particular vibration pattern that can be dictated by the application and/or vibrator in some cases.

When the external device 116 is placed within close proximity to the implantable device 104, the implantable device 104 can detect the vibration (e.g., via an accelerometer of the implantable device 104 as described in greater detail below) and determine whether to communicate with the external device 116 based on the detected vibration pattern. For example, the implantable device 104 can determine whether the vibration pattern corresponds to a vibration pattern identifier stored in or otherwise accessible by a memory of the implantable device 104. In either embodiment, the vibration pattern identifier can function as a secret password or key that can be referenced by the implantable device 104 to determine whether the external device 116 (or a user of the external device 116) requesting to establish a telemetry session with the implantable device 104 is authorized to communicate with the implantable device 104. As used in this disclosure, the term "user" can refer to a person, entity, device, system, or combination thereof.

In response to the implantable device 104 determining that the detected vibration pattern has a defined level of similarity (the level of which can be dictated by the designer of the implantable device 104 and/or can change from time to time or based on different conditions indicating greater or less security risk) with the vibration pattern identifier, the implantable device 104 can authorize and/or establish a telemetry session with the external device 116. For example, in some embodiments, after the implantable device 104 authorizes the external device 116 based on the vibration pattern generated by the external device 116, the implantable device 104 and the external device 116 can establish a secure communication channel between one another. In response to the implantable device 104 determining that the detected vibration pattern fails to have the defined level of similarity with the vibration pattern identifier, the implantable device 104 can forgo communication with the external device 116 or limit the type of communication that may take place.

The use of vibration of an external device 116 to facilitate authorization of a telemetry session between the external device 116 and the implantable device 104 can improve security of the information stored in the implantable device 104 since the external device 116 must typically be placed in close proximity of the implantable device 104 for detection of the vibration pattern. Therefore, during the authorization process, the patient wearing the implantable device 104 will typically closely interact with, or see, the user operating the external device 116.

In the example shown in system 100, the person operating the external device 116 is the patient wearing the implantable device 104. During the authorization process, the patient wearing the implantable device 104 can hold the external device 116 up to his/her body (e.g., at a location of the body 102 near where the implantable device 104 is located). In another example, another person (e.g., such as medical caregiver) interacting with the patient wearing the implantable device 104 can position the external device 116 near the implantable device 104 during the authorization process. Accordingly, if the wearer of the implantable device 104 does not trust the user operating the external device 116, the wearer of the implantable device 104 can reduce the likelihood of unauthorized pairing between the implantable device 104 and the external device 116 by moving away from the external device 116 and/or user operating the external device 116.

In various embodiments, the implantable device 104 can include any number of different types of implantable devices configured to detect a vibration pattern of an external device 116 and/or conduct a telemetry session with the external device 116 or another external device based on authorization of the vibration pattern. The particular, size, shape, placement and/or function of the implantable device 104 may not be critical to the subject disclosure in some embodiments.

In one embodiment, the implantable device 104 is or includes an IMD. For example, some example implantable devices can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, and/or drug delivery devices. In various embodiments, however, the implantable device 104 can be or include any number of other types of implantable devices that are not IMDs.

For exemplary purposes, the implantable device 104 is illustrated in system 100 as an IMD implanted within the chest of a patient and configured to provide medical treatment associated with a heart disease or condition (e.g., an implantable cardioverter-defibrillator (ICD), a pacemaker, etc.). The implantable device 104 includes a housing 106 within which electrical components and a power source are housed. These electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. Housing 106 can be formed from conductive materials, non-conductive materials or a combination thereof.

The implantable device 104 further includes leads 110*a,b* connected to the housing 106. The leads 110*a,b* extend into the heart and respectively include one or more electrodes. For example, as depicted in system 100, leads 110*a,b* each include a respective tip electrode 112*a,b* and ring electrode 114*a,b* located near a distal end of their respective leads 110*a,b*. When implanted, tip electrodes 112*a,b* and/or ring electrodes 114*a,b* are placed relative to or in a selected tissue, muscle, nerve or other location within the body 102 of the patient. As depicted in system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrode 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the implantable device 104 via connections in connector block 108.

In one or more embodiments, the implantable device 104 is configured to deliver therapy to the heart (or other location) via the electrical conductors to one or more of electrodes 112a,b and 114a,b. In the case of pacing therapy, for example, the implantable device 104 may deliver pacing pulses via a unipolar electrode configuration, e.g., using electrodes 112a,b and a housing electrode of the implantable device 104. In other instances, the implantable device 104 may deliver pacing pulses via a bipolar electrode configuration, e.g., using electrodes 112a,b and ring electrodes 114a,b. Implantable device 104 may also receive sensed electrical signals on the electrical conductors from one or more of electrodes 112a,b and 114a,b. The implantable device 104 may sense the electrical signals using either a unipolar or bipolar electrode configuration.

In one or more embodiments described herein, when authorized, an external device 116 can communicate with the implantable device 104 to exchange data with the implantable device 104. For example, the external device 116 can read data captured by the implantable device 104 (e.g., electromyography data) and/or remotely control/program the implantable device 104 (e.g., to adjust sensing, pacing therapy and/or defibrillation therapy). The implantable device 104 may also transmit sensed physiological data, diagnostic determinations made based on the sensed physiological data, implantable device 104 performance data and/or implantable device 104 integrity data to external device 116. The external device 116 and the implantable device 104 can communicate via wireless communication using any techniques known in the art. Examples of communication techniques can include, for example, inductive telemetry or RF telemetry, although other techniques are also contemplated.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances, take the form of a coil. The implantable device 104 can deliver defibrillation or cardioversion shocks to the heart via any combination of the elongated electrodes and housing electrode. As another example, the implantable device 104 can include leads with a plurality of ring electrodes, (e.g., as used in some implantable neurostimulators), without a tip electrode or with one of the ring electrodes functioning as the "tip electrode."

Implantable device 104 can include various different types of vibration sensors, electrodes and/or circuitry, configured to detect vibration activity of the external device 116 and the particular vibration pattern represented by the vibration activity. These sensors, electrodes and/or circuitry can include, but are not limited to, a piezoelectric sensor, piezoelectric circuitry and/or an accelerometer. As implantable device 104 is illustrated in system 100, by way of example, the vibration sensors and/or circuitry can be included within the housing 106 and/or in association with the various leads 110a,b and electrodes 112a,b and 114a,b of the implantable device 104.

Parameters representing motion detected by vibration sensors and/or circuitry can include, but are not limited to, displacement, velocity and/or acceleration. The motion can also be represented in terms of the amount of time during which the motion has occurred. The displacement, velocity and/or acceleration of the vibration activity can depend on a number of different factors including, but not limited to, frequencies of interest and/or signal power levels for the external device 116 or the like. The amount of time selected for the duration of a vibration activity can also depend on various factors, including but not limited to, a sufficient duration of time associated with establishing a unique vibration pattern, a sufficient duration to time associated with detecting the unique vibration pattern by the implantable device 104, a number of repetitions of the unique vibration pattern, and the like.

Vibration measurement sensors and/or circuitry can also detect and/or evaluate vibration frequency/intensity. One or more of these parameters (e.g., velocity and/or acceleration) can be measured from a variety of different types of vibration sensors. In some embodiments, the implantable device 104 can perform one or more operations to convert one measured value or set of information to another value or set of information based on known information and/or known relationships between the measured information and the desired information (e.g., relationship between velocity and acceleration). Selection of a sensor for inclusion in the implantable device 104 can be based on or otherwise proportional to expected or typical displacement, velocity, or acceleration of one or more different types of external devices, for example.

Vibration measurement sensors and/or circuitry can include a clock to associate a time component with respective measured vibration parameters. Using the clock, the vibration measurement sensors can determine the onset and the end point of a vibration activity. For example, the vibration activity can begin with an initial vibration behavior that is distinguishable from vibration behaviors associated with bodily functions or other natural occurring events. This initial vibration behavior can trigger recordation of the start time of the vibration activity. The vibration measurement sensors and/or circuitry can determine that a vibration activity has ended when vibration behaviors are no longer detected (e.g., a first vibration activity within the vibration pattern has ended; a cease vibration period within the vibration pattern has commenced; a vibration pattern has concluded; and/or when the vibration behaviors detected exhibit distinctions in intensity from those associated with the vibration activity).

In one embodiment, using one or more vibration sensors, the implantable device 104 is configured to detect and/or measure vibration activity in response to contact of the external device 116 with the body 102 of the wearer of the implantable device 104. In accordance with this embodiment, one or more vibration sensors of the implantable device 104 can measure the effect the vibration activity of an external device 116 has on the implantable device 104 within the body. For example, vibrations generated by the external device 116 when contacting the body 102 can resonate within the body. These vibrations resonating within the body can be measured by vibration sensors of the implantable device 104 and correlated to a vibration pattern identifier.

According to this embodiment, to facilitate detection of vibration activity of the external device 116, the external device 116 can be located within a detectable range of the implantable device 104 or otherwise positioned on or near enough to the body 102 in which the implantable device 104 is located. The detectable range can vary based on the type of the detection component located within the implantable device 104 since a first type of detection component can have greater or more sensitivity with regard to detection of vibration than other detection components. In some embodiments, the closer the external device 116 is placed near the implantable device 104 within the body (e.g., against the left side of the chest of the patient when the implantable device 104 is located near the heart 110, as depicted in system 100), the greater the likelihood of detection by the implantable device 104 and/or the greater the likelihood of accurate evaluation of the vibration pattern by the implantable device 104.

In another embodiment, implantable device 104 can include one or more non-contact displacement sensors to facilitate detecting vibration activity of an external device 116. Non-contact displacement sensors can be mounted with a gap between the sensor or sensing circuitry of the implantable device 104 and a surface of the vibrating object (e.g., the vibrating external device 116 and/or an internal body part receiving resonating vibrations in response to contact of the vibrating external device 116 with the body 102). Capacitive and eddy-current displacement sensors can provide high resolution displacement measurements. Vibration displacement data from these sensors can be differentiated to provide velocity information and differentiated a second time to obtain acceleration information. The differentiation process can limit low frequency signals and emphasize higher frequency signals, and can result in lower signal-to-noise ratios at higher frequencies. According to embodiments employing non-contact displacement sensors, therefore, the implantable device 104 can detect and determine a vibration pattern generated by an external device 116 when the external device is located within a fixed distance (e.g., less than a threshold distance) of the implantable device and potentially not touching/contacting the body 102.

Depending on the vibration sensors employed by the implantable device 104, the implantable device 104 can detect or determine vibration measurement data corresponding to displacement, velocity, acceleration, time period of and/or frequency for vibration activity generated by the external device 116. The implantable device 104 can then compare this vibration measurement data to information identifying one or more vibration patterns (e.g., vibration pattern identifiers) provided in memory of, or otherwise accessible by, the implantable device 104. In various embodiments, the vibration measurement data output can be generated and/or evaluated by circuitry designed to output specific types of information or electrical signal and/or can be communicated based on changes in mechanical features of one or more devices or circuits that can be included in the implantable device 104. In some embodiments, the vibration measurement data can be generated and/or evaluated based on one or more operations of computer executable components of the implantable device 104. In some embodiments, the implantable device 104 can process the vibration measurement data and generate a condensed digital or analog summary based on the vibration data that corresponds to a vibration pattern represented by the vibration data. In response to a determination that the vibration measurement data has a defined level of similarity/correlation with or otherwise corresponds, or substantially corresponds, to a vibration pattern identifier, the implantable device 104 can authorize, establish and/or participate in a telemetry session between the implantable device 104 and the external device 116. As discussed above, in an embodiment, the particular capacities of the telemetry session (e.g., read only, read and program, read classified data having a first level of sensitivity, read classified data having a second, higher level of sensitivity) can be determined and/or restricted by the implantable device 104 based on the particular vibration pattern detected and/or an iteration of a detected vibration pattern.

External device 116 can include any suitable computing device configured to generate a vibration pattern and communicate with implantable device 104. For example, external device 116 can include, but is not limited to, a handheld computing device, a mobile phone, a smart phone, a tablet personal computer (PC), a laptop computer, a desktop computer, a personal digital assistant (PDA) and/or a wearable device.

Existing cellular phones, smart phones, tablets, wearable devices and/or other handheld devices often include vibration hardware that is used to cause the respective devices to vibrate. A vibration is generally used by these devices as a signal to provide a notification to a user of the device. For example, a smart phone can be configured to vibrate as opposed to output an audible ring when a call is received. In one or more of the embodiments described herein, the vibration hardware of these devices can be controlled to generate one or more different vibration patterns.

In various embodiments, the external device 116 can include various circuitry, mechanical or electromechanical components configured to generate vibration activity. For example, the vibration hardware of the external device 116 can include various electrical and mechanical components and circuitry configured to generate vibration activity corresponding to specific vibration patterns with intricate variations in the intensity of the vibration (leading to differences in displacement), velocity, acceleration, time period and/or frequency of the vibration. An offset weight motor is an example of one suitable hardware component. The offset weight motor can include a rotational vibrator that is formed using a cylindrical body with a wedge cut out that spins on a motor. The vibration can be created by the imbalance of a counterweight. Another suitable vibration hardware component can include a piezoelectric bender. A piezoelectric bender can be actuated by a haptic driver or haptic controller integrated circuit (IC), or an oscillator at desired vibration frequency. In some embodiments, the external device 116 can include an eccentric rotating mass (ERM) vibration motor, also known as a pager motor. An ERM is a DC motor with an offset (non-symmetric) mass attached to the shaft. As the ERM rotates, the centripetal force of the offset mass is asymmetric, resulting in a net centrifugal force, and this causes a displacement of the motor. With a high number of revolutions per minute, the motor is constantly being displaced and moved by these asymmetric forces. This repeated displacement is perceived as vibration.

Another suitable vibration motor configured to generate vibration activity corresponding to a specific vibration pattern includes the linear resonance actuator (LRA). LRAs use a movable mass, permanent magnet, voice coil and spring to generate vibrations. The voice coil produces a magnetic field that interacts with the permanent magnet, causing the permanent magnet to move and by doing so, compresses or stretches the spring to which the magnet is attached. The drive signal alternates the direction of current and hence the magnetic field to make the permanent magnet oscillate back and forth with the spring. The moving mass is attached to the magnet, and the moving of the mass back and forth generates the vibration.

Because the subject vibration activity is performed from a combination of electrical and mechanical components and circuitry, and due to the specific combination of intensity, duration and pattern associated with a particular vibration pattern as described herein, a human is unable to replicate or perform the subject vibration activity. For example, the combination of electrical and mechanical components and circuitry can generate a specific and highly-accurate vibration pattern using variations of seconds or milliseconds between the vibrations within the pattern. These intricate and highly-specific vibration behaviors can be further synchronized to the expected vibration pattern identifier. In addition, the combination of electrical and mechanical components and circuitry can generate a specific intensity of the vibration and/or intensity over the vibration pattern that can be varied by different granularities over the course of the vibration pattern. Further, the combination of electrical and mechanical components and circuitry can generate several exact repetitions of these highly-technically specific vibration patterns. Recognition of the vibration pattern or a determination of correspondence between the vibration pattern and a vibration pattern identifier can be based on detection of a specific number of exact repetitions of the vibration pattern. Variance in vibration pattern repetition is inevitable when performed by a human and thus the embodiments described herein are not facilitated in many cases by human manually-attempted vibration activity.

As described herein, the one or more vibration patterns can be or include a combination of successive permutations of vibration on- and vibration off-patterns. The durations of time that the device is vibrating or ceasing to vibration during execution of the vibration pattern can vary from vibration to vibration and/or can change from time to time to create a number of possibilities for unique vibration patterns. In some embodiments, unique vibration patterns can also be generated as a function of vibration intensity/frequency. The term "vibration activity" is used herein to denote vibration of an external device 116 in accordance with a particular vibration pattern.

The characteristics/components of the vibration activity of which the vibration pattern is composed can be referred to as "vibration behaviors." In an embodiment, for example, a unique vibration pattern can include one or more defined vibration behaviors. For example, these vibrations behaviors can include, but are not limited to, vibration on-, vibration off-, duration of vibration on-, duration of vibration off-, successive and different durations of vibration on- and vibration off-patterns, a time period associated with a sequence of two or more vibrations, intensity of vibrations, or intensity variation between a sequence of two or more vibrations. By way of example but not limitation, a vibration pattern can include or be the following successive vibration behaviors over a total duration of a defined number of seconds (e.g., 16 seconds): vibrate at intensity level one for a duration of two seconds; cease vibration for one second; vibrate at intensity level two for three seconds; vibrate at intensity level one for three seconds; cease vibration for two seconds; and vibrate at intensity level four for five seconds.

One or more of the embodiments described herein can consider a vibration pattern generated by an external device 116 a password or secret key that is offered by the external device 116. The implantable device 104 can evaluate the vibration pattern to determine whether to authorize or conduct telemetry between the external device 116 and the implantable device 104. In accordance with one or more of these embodiments, the implantable device 104 is configured to detect vibration activity of an external device 116, determine a vibration pattern associated with the vibration activity, and compare the vibration pattern to a vibration pattern identifier known to or otherwise accessible to the implantable device 104. In response to a determination that the detected vibration pattern corresponds to, or substantially corresponds to, the vibration pattern identifier, the implantable device 104 can establish a telemetry session with the external device 116.

In some embodiments, individual users and/or external devices 116 can be assigned unique vibration patterns and the implantable device 104 can evaluate the unique vibration patterns based on unique vibration pattern identifiers assigned to the individual users and/or external devices. Thus, a first vibration pattern identifier can allow a first external device to communicate with the implantable device 104 while the same vibration pattern identifier may not allow a second external device to communicate with the implantable device 104. For example, the wearer of the implantable device 104 can be given (or select) a unique vibration pattern and associated vibration pattern identifier that is used to authenticate the wearer in association with establishing an authorized telemetry session with his/her implantable device 104. The unique vibration pattern identifier can be programmed into the implantable device 104 (e.g., stored in memory of the implantable device 104) and known to the wearer of the implantable device 104. By contrast, another user or group of users (e.g., medical caregiver or group of medical caregivers) not wearing the implantable device 104 can use a different vibration pattern and have a different associated vibration pattern identifier that will allow establishment of a telemetry session with the implantable device 104.

In another embodiment, different vibration patterns can be used to enable/authorize different types of communication and/or access to an implantable device 104 by an external device 116. For example, external device 116 can be used to read information from an implantable device 104 using telemetry. For instance, when the implantable device is an ICD, the information can include information regarding the patient's heartbeat, such as electromyography data. In another example, an external device 116 can be used to program or control an implantable device 104. For instance, when the implantable device 104 is a drug delivery device, external device 116 can employ telemetry to adjust a drug dosage provided by the implantable device 104. In accordance with this embodiment, different types of communication and access between an implantable device 104 and an external device 116 can be authorized based on different vibration patterns or based on iterations of vibration patterns.

For example, the implantable device 104 can allow communication of a first set of information (e.g., information rated as mildly sensitive) to the external device 116 yet deny communication of a second set of information (e.g., information rated as highly sensitive) when authorization of telemetry is based on a first vibration pattern. By contrast, the implantable device 104 can be programmed to authorize transfer of both the first and second sets of information when authorization of telemetry is based on a second vibration pattern. In some embodiments, the implantable device 104 can be configured to authorize programming of/changing operational parameters of the implantable device 104 (or, in embodiments in which the implantable device 104 is not the IMD, authorize programming of the IMD) by the external device 116 when authorization is based on a particular iteration of vibrations approved by the implantable device 104.

In yet another embodiment, two or more successive vibration patterns can be used to provide a greater level of security in association with accessing an implantable device 104. For example, implantable device 104 can be configured to require two successive valid vibration patterns from an external device 116 before allowing an external device 116 to establish a secure telemetry session with the implantable device 104.

In some embodiments, an implantable device 104 can be configured to facilitate one of a plurality of levels of access/communication with the external device 116 based on a determination as to whether a detected vibration pattern corresponds to a first iteration of vibration activity or another (e.g., second, third, fourth, etc.) iteration of vibration activity. For example, implantable device 104 can be configured to authorize an external device 116 to only read data from the implantable device 104 in response to detection of a particular, defined vibration pattern (e.g., vibration pattern A) provided by the external device 116. The implantable device 104 can further be configured to authorize the external device 116 to read data from the implantable device 104 and program/control a function of the implantable device 104 in response to detection of a first particular, defined vibration pattern followed by a second particular, defined vibration pattern (e.g., vibration pattern A followed by detection of vibration pattern B). In various embodiments, the first defined vibration pattern and the second defined vibration pattern can be distinct from one another or the same as one another. All such embodiments are envisaged.

Implantable device 104 and external device 116 can employ various wireless communication protocols to communicate with one another in association with an authorized telemetry session. For example, external device 116 and implantable device 104 can communicate using near field communication (NFC). In another example, external device 116 and implantable device 104 can communicate using any of various types of wireless communication protocols. For example, other communication protocols that can be employed by external device 116 and implantable device 104 to perform telemetry can include, but are not limited to, a BLUETOOTH® technology-based protocol (e.g., BLUETOOTH® low energy (BTLE) protocol), an ultra-wideband (UWB) technology-based protocol, a radio frequency (RF) communication-based protocol, or any other proprietary or non-proprietary communication protocols.

In various embodiments, communication can be facilitated over a personal area network (PAN), a local area network (LAN) (e.g., a Wireless Fidelity (Wi-Fi) network) that can provide for communication over greater distances than the NFC protocol or provide other advantages (e.g., stronger encryption protocols). In some embodiments, the external device 116 and implantable device 104 can communicate with one another and/or another device (e.g., a server device or a tertiary device) over a wide area network (WAN) using cellular or Hyper Text Transfer Protocol (HTTP)-based communication protocols (e.g., session initiation protocol (SIP)).

FIGS. 2A and 2B illustrate respective block diagrams of example, non-limiting systems depicting generation and detection of vibration patterns facilitating telemetry with an implantable device based on vibration of an external device in accordance with one or more embodiments described herein. Repetitive description of like elements employed in other embodiments described herein is omitted for sake of brevity.

Both systems 200 and 201 include an external device 116 that is configured to vibrate and an implantable device 104 that is configured to detect or sense the vibration activity of the external device 116. As shown, external device 116 is vibrating and the implantable device 104 is detecting or sensing the vibration activity of the external device 116.

In system 200, the external device 116 performs a first vibration activity and vibrates in accordance with a first vibration pattern, which is represented visually in the drawing by first vibration pattern data 204. The implantable device 104 detects the first vibration pattern and compares the first vibration pattern to a first vibration pattern identifier stored in memory 202 of, or otherwise accessible to, the implantable device 104. In response to a determination by the implantable device 104 that the first vibration pattern has a defined level of similarity/correspondence to/correlation with (or otherwise is deemed to match) the first vibration pattern identifier, the implantable device 104 authorizes, establishes and/or conducts a telemetry session with the external device 116.

For example, the implantable device 104 can detect one or more vibration parameters over the duration of the first vibration activity (represented visually by first vibration pattern data 204) using one or more vibration sensors (e.g., a piezoelectric sensor, an accelerometer, a displacement sensor, etc.). These vibration parameters can include velocity, acceleration, displacement, intensity and/or time duration of one or more vibration activities within a vibration pattern (and/or the time duration of the entire vibration pattern). The detected vibration parameters can be collectively referred to herein as the "vibration data." In an embodiment, the implantable device 104 can identify a pattern in the vibration data, referred to as the first vibration pattern. The implantable device 104 can then compare the first vibration pattern to a first vibration pattern identifier stored in memory 202.

In system 201, the external device 116 performs a second vibration activity and vibrates in accordance with a second vibration pattern. The implantable device 104 detects the second vibration pattern and compares the second vibration pattern to a second vibration pattern identifier stored in memory 202 of the implantable device 104. In response to a determination that the second vibration pattern has a defined level of similarity/correspondence to/correlation with (or otherwise is deemed to match) the second vibration pattern identifier, the implantable device 104 authorizes, establishes and/or conducts a telemetry session with the external device 116.

In some embodiments, the second and first vibration patterns represent two unassociated vibration activities by the external device 104. For example, the first vibration pattern data 204 can be closely matched to a particular vibration pattern identifier that allows the external device 116 to communicate with the implantable device 116, and thus communication can be allowed. By contrast, the second vibration pattern data 206 can be highly-distinct from the particular vibration pattern identifier that allows the external device 116 to communicate with the implantable device 116, and thus communication can be denied.

In some embodiments, the second vibration pattern occurs after the first vibration pattern in a sequence of vibration activity by the external device 116. The type of communication authorized can be based on whether the vibration pattern is the first iteration of vibration activity, the second iteration of vibration activity or another iteration in the sequence of one or more vibration activities. The external device 116 can provide the sequential vibration activity to gain greater access to the implantable device 104 for example. As such, the second vibration pattern can be a second iteration of vibration activity of the external device 116 (and the first vibration pattern can be the first iteration of vibration activity of the external device 116).

In this embodiment, for example, a first level of communication (e.g., initiation of a telemetry session) between the implantable device 104 and the external device 116 can be facilitated based on a determination that a particular vibration activity has the defined correlation with a particular vibration pattern identifier, and that the particular vibration activity is the first iteration of vibration activity. By contrast, a second level of communication (e.g., programming or changing an operation of the implantable device 116 or an implantable device associated with the implantable device 116) can be based on the determination that a particular vibration activity has the defined correlation with a particular vibration pattern identifier, and based on the determination that the particular vibration activity is the second iteration of vibration activity.

Figure 3A:
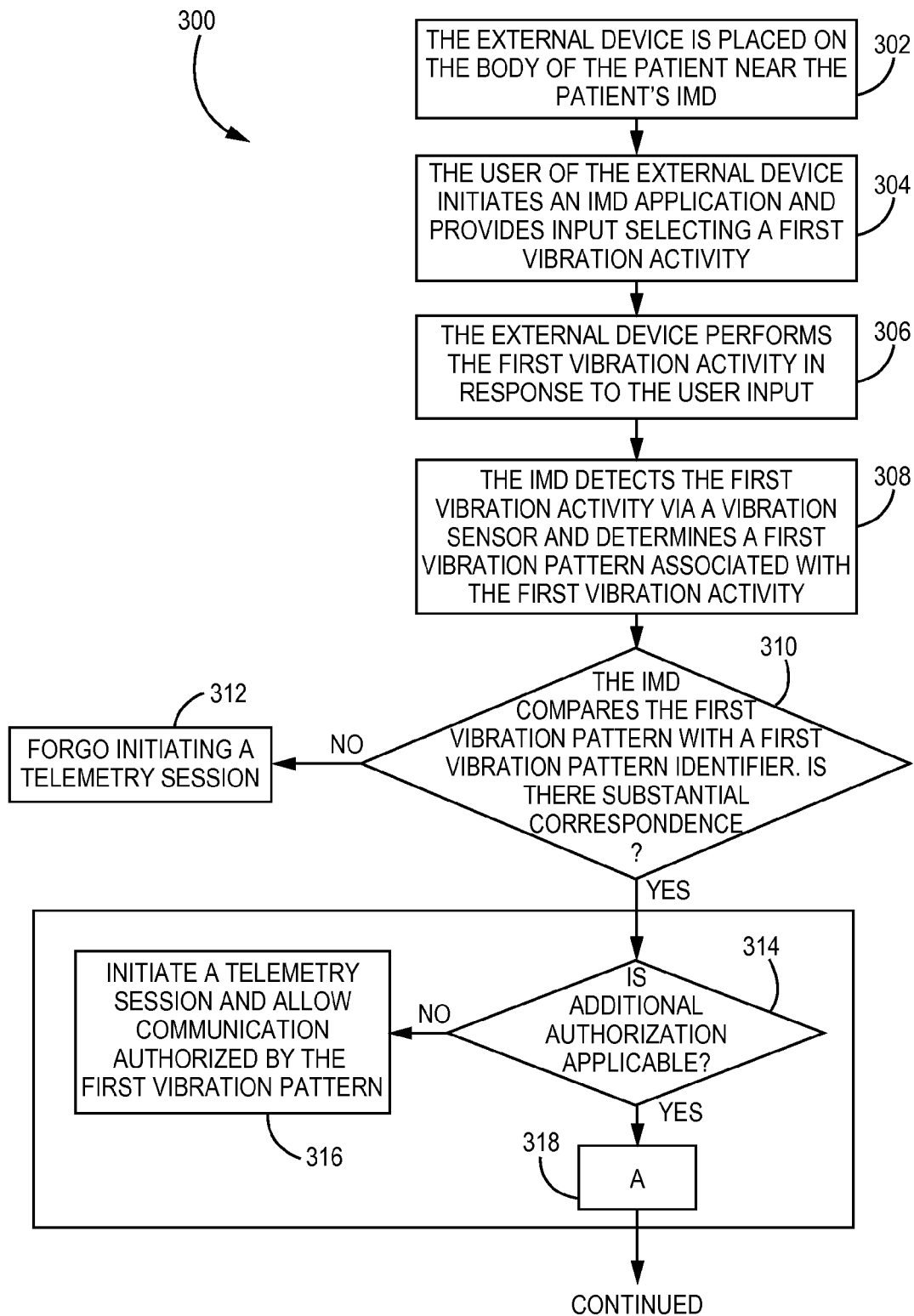
FIGS. 3A and 3B illustrate a flow chart of an example, non-limiting method of facilitating telemetry with an implantable device and an external device in accordance with one or more embodiments described herein.
Figure 3B:
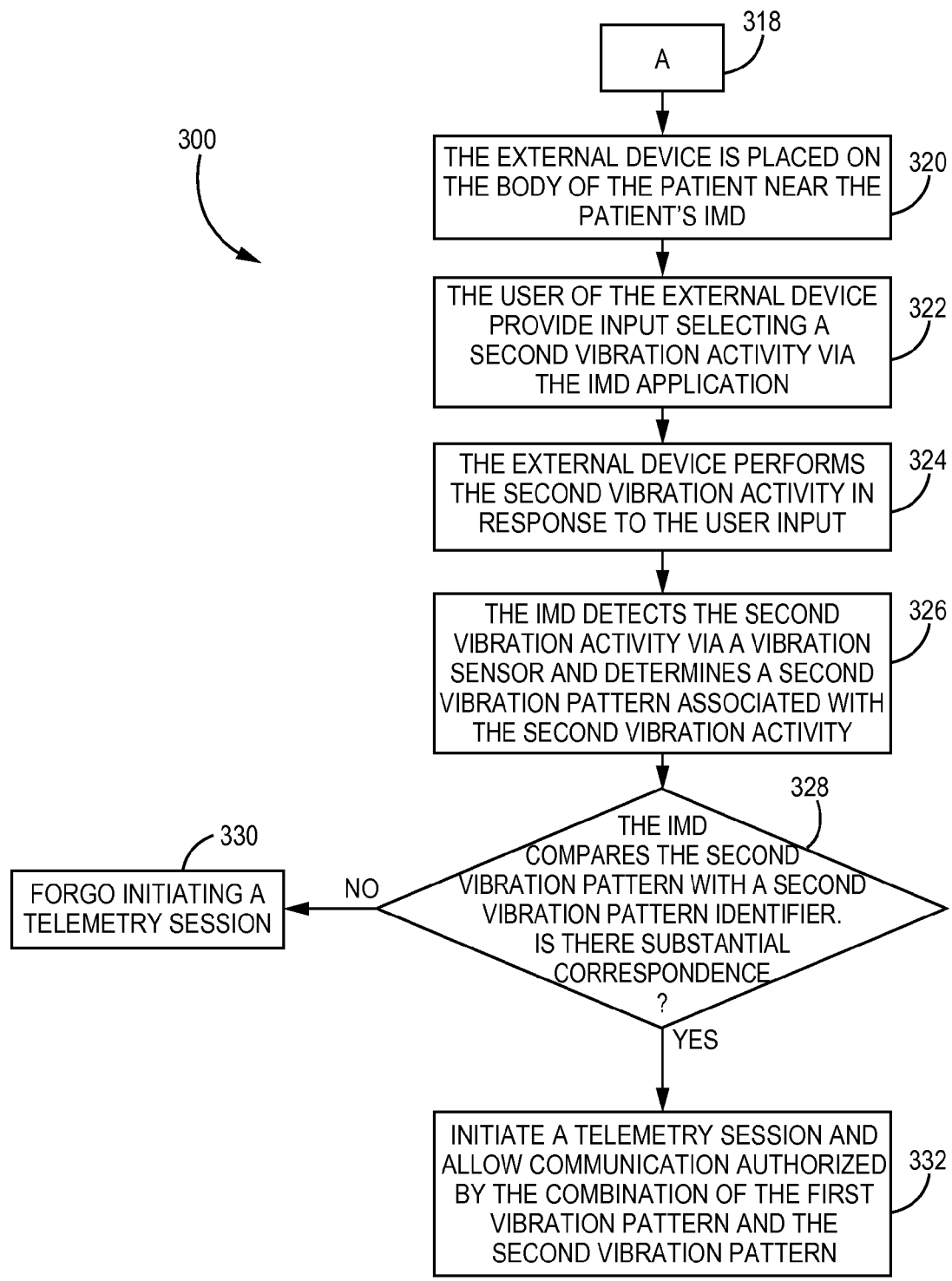

FIGS. 3A and 3B illustrate a flow chart of an example, non-limiting method 300 of facilitating telemetry with an implantable device and an external device in accordance with one or more embodiments described herein. Repetitive description of like elements employed in other embodiments described herein is omitted for sake of brevity.

Method 300 begins with FIG. 3A at 302 with placement of an external device (e.g., external device 116) on the body of a patient near the patient's implantable device (e.g., IMD). For example, the patient wearing the IMD or another person (e.g., the doctor of the patient), can hold a device configured to vibrate in accordance with a particular vibration pattern against the body of the patient so that the vibration is able to be detected by the IMD. In some embodiments, although not shown, placement of the external device can be provided via a positioning device or robot configured to move/locate the external device to a precise and/or defined position on or relative to the body of the patient and/or relative to the implantable device within a patient.

At 304, the user of the external device initiates an IMD application stored on or accessible by the external device and provides input selecting a first vibration activity or causing a first vibration activity to occur. For example, the external device can include an application or functionality that allows the user of the external device to interact with the IMD. For instance, the application can facilitate reading information from the IMD or programming/controlling the IMD. In one embodiment, the application or functionality can be programmed into the external device prior to provision to the end user by the external device manufacturer. In another embodiment, the application or functionality can be downloaded to the external device via a network from a mobile application distribution platform or application store, such as the iOS App Store and Android Google Play.

The application can also support the subject vibration-based authorization technique to facilitate establishing an authorized telemetry session between the external device and the IMD to allow for communication of data between the external device and the IMD. For example, the IMD application stored and executed on the external device can include or facilitate access to information defining the specific vibration pattern activity to be executed by the external device in order to establish an authorized telemetry session with the IMD. In some embodiments, to establish the authorized telemetry session using the functionality provided by the application, the application can require the user of the application to authenticate the user's (or the external device's) identity to verify the user and/or the external device is registered and authorized to employ the functionality of the application to communicate with the IMD. For example, the user can log into the IMD application on the external device and provide security information (e.g., username/password), which is relayed to a remote server device configured to authenticate the user/external device based on the security information. After the user/external device has been authenticated, the user can employ the functionality of the application, including one or more of the vibration-based authorization techniques described herein.

According to this embodiment, the application can provide access to information defining the vibration activity for performance by the external device that facilitates authorization of the external device by the IMD. For example, after the user has logged into the application, the application can access and/or download the information defining the specific vibration activity from the remote server via a network. In another embodiment, information defining the specific vibration activity can be programmed into the application and stored in memory of the external device with the application. According to this embodiment, the user of the external device can access and select information defining the specific vibration activity without communicating with a remote server device via a network.

While step 304 is indicated as a user initiating the IMD application, in some embodiments, the IMD application can be automatically initiated without human interaction based on any number of factors including, but not limited to, time of day, day of week, week of month, date, proximity of the external device to the IMD, proximity of the external device to a particular sensor that can be associated with a particular location (e.g., sensor at a doctor office) or the like.

At 306, the external device performs the first vibration activity in response to the user input. In some embodiments, the external device performs the first vibration activity in response to the activation of the IMD application or initiation (either with or without human input to the external device and/or IMD application of the external device).

At 308, the IMD detects the first vibration activity via one or more vibration sensors or circuitry (e.g., an accelerometer), and determines a first vibration pattern associated with the first vibration activity. For example, the IMD can sense vibration data related to velocity, displacement, acceleration and/or intensity over the duration of the first vibration activity. The IMD can then process the vibration data to identify or characterize one or more vibration behaviors represented by the data, and more particularly a pattern represented by the one or more vibration behaviors (e.g., as a function of time).

At 310, the IMD compares the first vibration pattern with a first vibration pattern identifier and determines whether the first vibration pattern has a defined level of correspondence to the first vibration pattern identifier. In response to a determination that the first vibration pattern has the defined level of correspondence to the first vibration pattern identifier, method 300 can continue to step 314. In response to a determination that the first vibration pattern does not have a defined level of correspondence to the first vibration pattern identifier, at 312, the method 300 forgoes initiation of a telemetry session between the IMD and the external device.

For example, the first vibration pattern identifier can define a pattern of vibration behaviors and the IMD can compare the vibration behaviors determined for the first vibration activity with the vibration behaviors defined by the first vibration pattern identifier. If the vibration behaviors determined for the first vibration activity and the vibration behaviors defined by the first vibration pattern identifier exhibit a threshold degree of similarity (e.g., 100% match, 95% match, 75% match, etc.) then method 300 can continue to step 314. If the vibration behaviors determined for the first vibration activity and the vibration behaviors defined by the first vibration pattern identifier do not exhibit the threshold degree of similarity then method 300 ends at step 312.

At 314, the IMD and/or the external device determine whether additional authorization is applicable prior to initiating a telemetry session with the external device. In some cases, various levels of access to the IMD can be associated with different vibration activities or performance of a sequence of different vibration activities. For example, step 318 can be applicable in a situation in which the IMD is programmed to authorize a telemetry session only in response to reception of two successive different vibration activities that match respective corresponding vibration pattern identifiers. In another example, step 318 can be applicable in a situation in which the IMD is programmed to authorize a first form of communication (e.g., read only) based on a first iteration of an approved vibration pattern and programmed to authorize a second form of communication (e.g., read and program the IMD) based on a second iteration of approved vibration pattern.

Therefore, depending on the type of access desired by the external device, additional authorization can be applicable. For example, in accordance with method 300, additional authorization is applicable when the external device (or user of the external device) wants to program or remotely control the functionality of the IMD. If the external device attempts to use this functionality (e.g., perform programming or remote control of the functionality of the IMD) after provision of only the first vibration activity (e.g., first iteration of vibration activity), while the first vibration activity can be determined to be satisfactorily correlated with a first vibration pattern identifier, since the vibration activity is only a first iteration of activity (instead of a second iteration of approved vibration pattern, for example), the IMD can reject the attempt by the external device to perform more extensive functionality relative to the IMD. The external device can receive an error message (e.g., facilitated by the IMD application). The error message can indicate that additional authorization is required. In the event that the external device or the user of the external device has access to or is able to provide the information required for the additional authorization (e.g., a second vibration activity has been determined to be satisfactorily correlated with a second vibration pattern identifier), method 300 can proceed to 318, which directs the IMD/external device to continue method 300 in accordance with track A shown in FIG. 3B. In response to a determination that additional authorization is not applicable (e.g., because the type of communication desired by the external device is authorized by the first vibration pattern), method 300 can proceed to 316 and the IMD can initiate a telemetry session with the external device and allow communication authorized by the first vibration pattern. In some embodiments, although not shown, telemetry may be pre-existing between the external device and the IMD and, at 316, telemetry may be authorized to continue (in lieu of being initiated) in response to a determination that the vibration pattern is satisfactorily correlated with a vibration pattern identifier.

Track A includes repetition of previous steps with the substitution of the first vibration activity with a second vibration activity. At 320, the external device is placed on the body of the patient near the patient's IMD. At 322, the user of the external device provides input selecting a second vibration activity via the IMD application. At 324, the external device performs the second vibration activity in response to the user input. At 326, the IMD detects the second vibration activity via a vibration sensor and determines a second vibration pattern associated with the second vibration activity. At 328, the IMD compares the second vibration pattern with a second vibration pattern identifier and determines whether there is correspondence between the second vibration pattern and the second vibration pattern identifier. In response to a determination that there is insufficient correspondence between the second vibration pattern and the second vibration pattern identifier, method 300 ends at 330 at which the telemetry session is forgone (or only the first level of telemetry, which is authorized by the correspondence between the first vibration pattern and the first vibration pattern identifier, is approved). In response to a determination that there is sufficient correspondence between the second vibration pattern and the second vibration pattern identifier, method 300 ends at 332 and a telemetry session is initiated that allows communication authorized by the second vibration pattern and the first vibration pattern (e.g., remote control or programming of the IMD by the external device). It should be appreciated that method 300 can be repeated in several iterations to provide for a degree of authorization activity considered appropriate to obtain a desired level of security.

Although method 300 separates the input associated with generating a first vibration activity and generating a second vibration activity (and therefore presents two instances of vibration activity being initiated at the external device), in one or more embodiments, a single input can be used to generate two or more separate vibration patterns in sequence without an intervening activation at the external device for a second vibration pattern. For example, in association with a request to gain a particular level of access to an implantable device that is associated with a combination of two or more vibration patterns (e.g., standard communication and programming of the IMD), the external device can receive input identifying the particular level of access desired. Based on the input, the external device IMD application or the external device generally can interpret the request as a command to generate a sequence of two or more unique vibration patterns in sequence (e.g., a first vibration pattern and a second vibration pattern). These unique vibration patterns can be programmed into memory of the external device or accessible by the IMD application (e.g., via a user account a user of the IMD application is currently signed into). The IMD can detect that both vibration patterns have been provided and determine whether there is satisfactory correspondence between each of the vibration patterns and the corresponding vibration pattern identifiers. If satisfactory correspondence is determined for both vibration patterns, the IMD can initiate and/or perform telemetry and allow programming and/or control in association with the control indicated by the first vibration pattern and the second vibration pattern.

Figure 4:
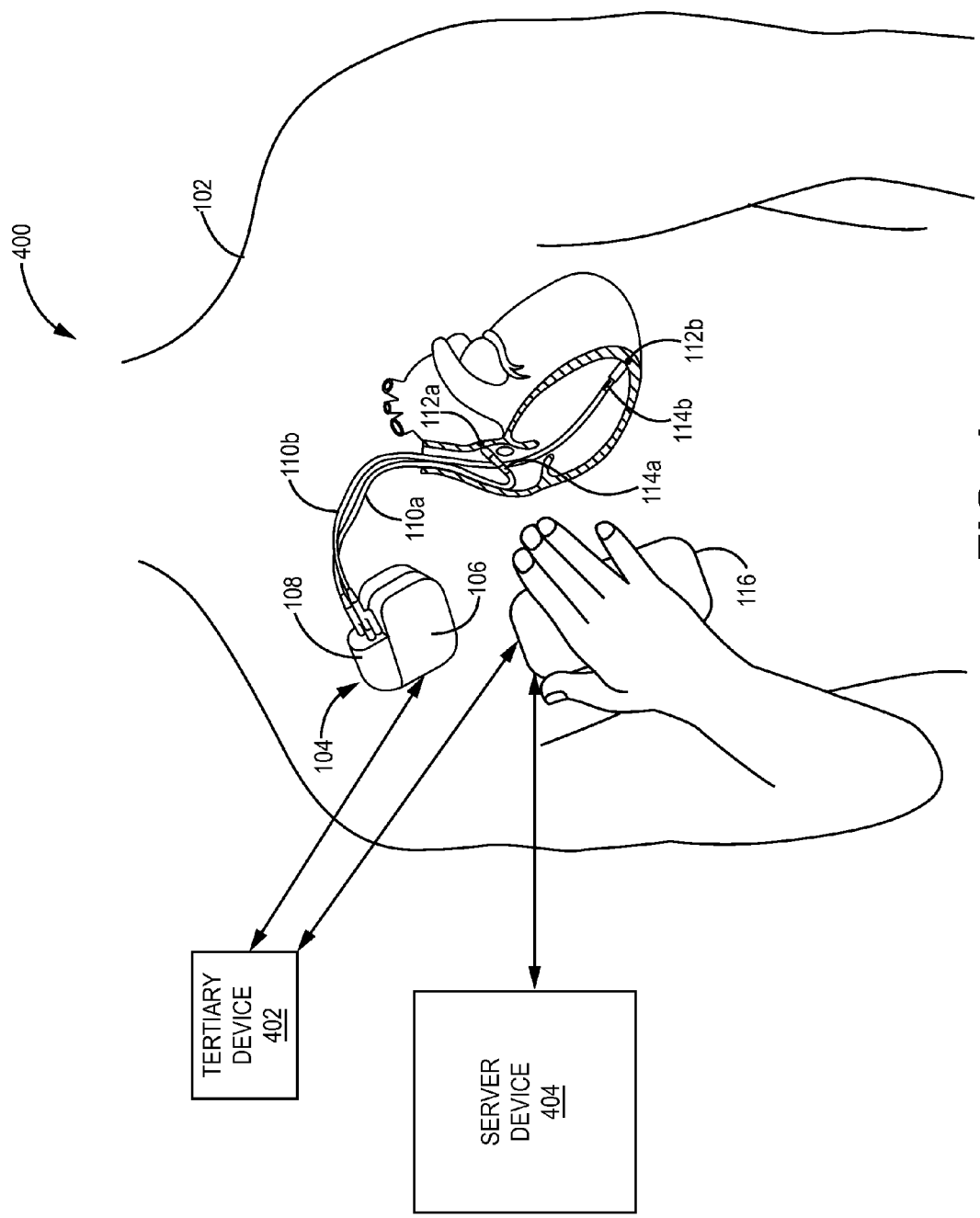
FIG. 4 illustrates another example schematic diagram of an example, non-limiting medical device telemetry system facilitating telemetry with an implantable device based on vibration of an external device in accordance with one or more embodiments described herein.

FIG. 4 illustrates another example schematic diagram of an example, non-limiting medical device telemetry system facilitating telemetry with an implantable device based on vibration of an external device in accordance with one or more embodiments described herein. System 400 includes the various structure, features and functionalities as system 100 with the addition of a tertiary device 402 and a server device 404. Repetitive description of like elements employed in other embodiments described herein is omitted for sake of brevity.

The various devices of system 400 can be configured to communicate with one another using a variety of networks (not shown) and wireless communication protocols. For example, the devices of system 400 can communicate using any of a variety of types of communication protocols over a PAN or a LAN, (e.g., a Wi-Fi network) that may provide for communication over greater distances than the communication protocol typically provides and/or provide other advantages (such as increased security). Communication protocols that can be employed by system 400 can include, but are not limited to, BLUETOOTH® technology-based protocols (e.g., BTLE protocol), NFC, UWB standard protocols, RF communication protocols, and/or other proprietary and nonproprietary communication protocols. In another embodiment, the devices of system 400 can communicate with one another (and/or another device) over a WAN using cellular or HTTP based communication protocols (e.g., SIP).

In an embodiment, external device 116 is configured to communicate with a server device 404 via one or more of the networks described above. For example, the external device 116 can receive information indicative of instructions dictating a particular vibration pattern by which the external device 116 is to vibrate. As another example, after the external device 116 and the implantable device 104 have established an authorized telemetry session using the vibration-based authorization method described herein, the external device 116 can communicate data between the implantable device 104 and the server device 404 via a network. This data can include, but is not limited to, control commands issued by the server device 404 sent from the server device 404 to the implantable device 104 via the external device 116. In another embodiment, the data can also include information transmitted from the implantable device 104 to the server device 404 via the external device 116.

In some embodiments, the implantable device 104 and the external device 116 can communicate via different networks. For example, the implantable device 104 and the external device 116 can communicate via a first network (e.g., a PAN, or LAN) and the external device 116 and the server device 404 can communicate via a second network (e.g., a WAN).

In some embodiments, the server device 404 can store computer-readable storage media on which instructions facilitating operations of an application service provider can be stored. The application service provider can be configured to facilitate operations of an IMD application provided on the external device 116 that can be employed by the external device 116 to interact with the implantable device 104.

Figure 5:
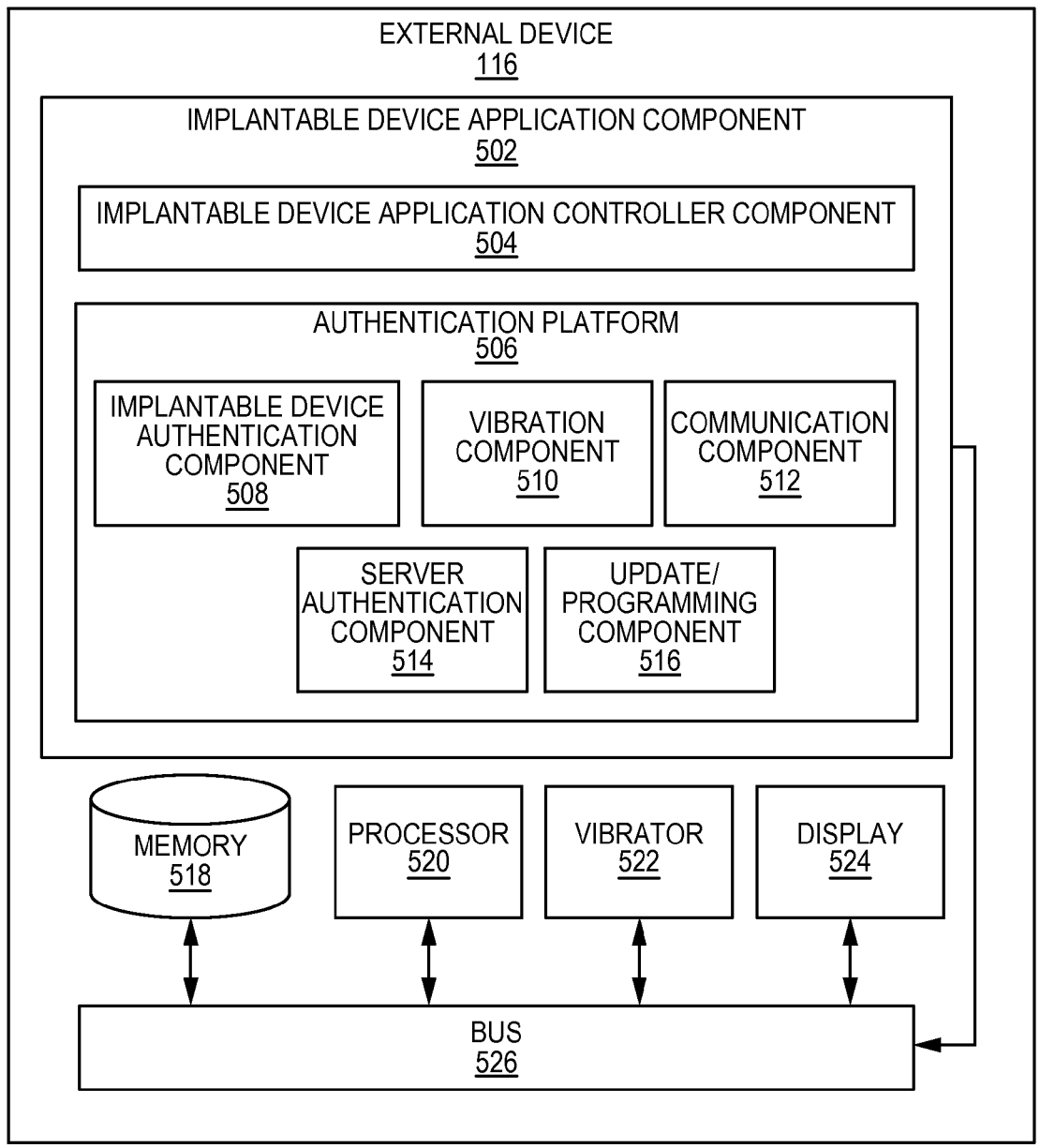
FIG. 5 illustrates an example, non-limiting block diagram of an external device configured to execute a vibration-based authentication process to facilitate establishing a telemetry session with an implantable device in accordance with one or more embodiments described herein.

FIG. 5 illustrates an example, non-limiting block diagram of an external device configured to execute a vibration-based authentication process to facilitate establishing a telemetry session with an implantable device in accordance with one or more embodiments described herein. Repetitive description of like elements employed in other embodiments described herein is omitted for sake of brevity.

For example, with reference to FIGS. 4 and 5, the external device 116 can include an implantable device application component (e.g., implantable device application component 502) that can facilitate interacting with an implantable device (e.g., implantable device 104) in a variety of manners (e.g., reading and displaying information read from the implantable device, programming the implantable device, controlling functions of the implantable device, etc.). In some embodiments, the implantable device application component 502 can also include functionality to cause the external device 116 to perform the subject vibration-based authorization method to enable authorized communication between the implantable device and the external device 116 (or another device such as tertiary device 402).

According to this embodiment, the server device 404 can provide additional security in association with establishing an authorized telemetry session between the implantable device 104 and the external device 116 (or another device) by using an authentication method. The authentication method can be employed between the server device 404 and the user of the external device 116 before allowing the implantable device application component 502 to be activated and/or used.

For example, the server device 404 can provide different users a variety of services associated with the implantable device application component 502. For instance, when the implantable device 104 is or includes an IMD, one of these services can include retaining and/or providing access to patient health information/records associated with the IMD of the patient. Another one of these services can include managing access to implantable devices by different users.

In association with managing access to implantable devices by different users, the respective users can establish user accounts with the server device 404. The users can access their respective user accounts via the implantable device application component (e.g., implantable device application component 502) provided on their respective external devices (e.g., external device 116). In an embodiment, the respective user accounts can be associated with personal information for the respective users. This personal information can include, but is not limited to, information regarding the implantable device or one or more external devices the implantable device is authorized to access. The personal information can also include, but is not limited to, information indicative of the manner in which the external device can access/communicate with the implantable device (e.g., read information at the implantable device only; read information at the implantable device and program one or more aspects of the implantable device). The personal information can also include, but is not limited to, data defining the vibration activity that is required to access the implantable device or devices. For example, a doctor can have a user account that includes information identifying all the IMDs for the different patients of the doctor, information defining the vibration activity (or activities) required for establishing an authorized telemetry session with the respective IMDs for different patients, and/or information describing the particular type of telemetry session/level of access associated with the respective vibration activity (or activities).

In some embodiments, the server device 404 can require users to sign in to the respective user accounts in order to access the user accounts and/or personal information associated with the respective user accounts. In some embodiments, the server device 404 can require the users to sign in to the respective user accounts prior to allowing the users to access the vibration-based authorization functionality provided by the implantable device application component 502. Server device 404 can employ various user authentication/authorization protocols to perform the secure sign in procedure. For example, server device 404 can employ a username and password system, an external authorization system, a single sign-on service, a public key infrastructure system (PKI), etc.

For example, after a user of external device 116 signs in to implantable device application component 502 on the external device 116, the user can use the application to facilitate establishing a secure telemetry session between the external device 116 and the IMD (e.g., implantable device 104). For instance, the user can select information identifying the IMD and/or the unique vibration activity associated with access to his IMD as provided in the personal user account in association with a request to establish a telemetry session with the IMD. In response to selection of the information identifying the IMD and/or the unique vibration activity associated with access to his IMD, the external device 116 can perform the unique vibration activity (e.g., vibrate according to the unique vibration pattern corresponding to the unique vibration activity).

In some embodiments, in order to access the vibration-based authorization functionality provided by the application, the server device 404 can be configured to require the implantable device application component 502 (or external device 116) to have an active signed-on session with the server device 404 (e.g., be connected to the server device 404 via the Internet). According to this embodiment, the external device 116 is connected to the server device 404 via a network in order to perform and/or complete the vibration-based authorization actions (e.g., vibrating according to a defined vibration pattern for detection and possible approval by the implantable device 104).

In another embodiment, after signing on, the external device 116 can download information defining the unique vibration activity associated with access to a particular implantable device 104. This information can later be utilized and/or employed by the external device 116 when the external device is not connected to the server device 404 via a network (e.g., offline) to perform the vibration-based authorization method described herein.

In another embodiment, as shown in FIG. 4, the implantable device 104 can be configured to communicate with a tertiary device 402 via one or more networks described with reference to FIG. 4. According to this embodiment, the external device 116 can perform one or more of the vibration-based authorization methods described herein. However, in response to the vibration-based authorization method performed between the external device 116 and the implantable device 104, the implantable device 104 can be configured to establish an authorized telemetry session with a tertiary device 402. Accordingly, in this embodiment, the tertiary device 402 need not have vibration capabilities that enable the tertiary device 402 to perform vibration activity. Also with this embodiment, the tertiary device 402 (as opposed to the external device 116) can communicate with the implantable device 104 via a network in accordance with the authorized telemetry session. This communication can include reading data from the implantable device 104 and/or programming or controlling the implantable device 104. The tertiary device 402 can include any suitable computing device configured to communicate with implantable device 104 using a wireless communication protocol. For example, in some embodiments, the tertiary device can be or include any of the devices described with reference to the external device 116. For example, tertiary device 402 can be mobile or stationary and/or can include, but is not limited to, a handheld computing device, a mobile phone, a smart phone, a tablet PC, a laptop computer, a desktop computer, a server computer, or a PDA.

Turning back to FIG. 5, as shown, in one embodiment, the external device 116 can include an implantable device application component 502 configured to facilitate interacting with an implantable device 104 in a variety of manners as described above with respect to system 400. External device 116 can also include memory 518 that stores computer executable components, and a processor 520 that executes the computer executable components (e.g., the implantable device application component 502 and/or the various components of the implantable device application component) stored in the memory. External device 116 further includes a display 524 and vibrator 522 configured to cause the external device 116 to perform one or more vibration activities based on information associated with the vibration activities defining the vibration behaviors and/or patterns of the vibration activities. External device 116 can include a bus 526 that couples the various external device 116 components including, but not limited to, implantable device application component 502 (and the various components of the implantable device application component 502), memory 518, processor 520, vibrator 522, and display 524. In various embodiments, the vibrator 522 can be a device or circuitry that generates a vibration of the external device.

In some embodiments, external device 116 can also include a display 524 configured to provide an interface to a user of the device, or to another device configured to read the display 524. For example, the display 524 can be a touch screen display in some embodiments. In some embodiments, the display 524 can be a component that outputs a visual, audible or other indicator of information. The display 524 can facilitate activation and/or utilization of the various functionalities of the external device 116 (e.g., using the implantable device application component 502, displaying information received from an implantable device 104, issuing control commands to the implantable device 104, issuing commands to change the parameters or otherwise program or re-program the implantable device 104).

Implantable device application component 502 can include the various features and functionalities discussed in association with one or more embodiments of the implantable device application component 502 in association with system 400. In some embodiments, the implantable device application component 502 can include the implantable device application controller component 504 and authentication platform 506.

The implantable device application controller component 504 can facilitate one or more of a variety of potential application functions afforded by the implantable device application component 502 that may be unrelated to authentication/authorization of telemetry between the external device 116 and the implantable device 104. For example, these functions can include, but are not limited to, those associated with facilitating interfacing between the implantable device 104 and the external device (e.g., reading/receiving data from the implantable device 104 and/or controlling or programming the implantable device after a telemetry session has been authorized via the vibration-based authorization techniques described herein). In another example, these functions can facilitate interfacing between the external device 116 and the server device 404 in one or more ways as described herein. In another example, these functions can facilitate remote storing and/or tracking of patient medical information as relates to the IMD (e.g., cloud-based computing functionalities).

Authentication platform 506 can be configured to facilitate the various authorization and authentication functions described herein Implantable device authentication component 508 can be configured to facilitate authorization of a telemetry session between the implantable device 104 and external device 116 (or a tertiary device 402) using the vibration-based authorization techniques described herein.

In particular, the implantable device authentication component 508 can receive and/or process a request to attempt to establish a telemetry session with implantable device 104. The request can identify the particular implantable device and/or a particular vibration activity. The request can identify a type of communication authorized for the telemetry session (e.g., read only, read and program). In some embodiments, the information included in the request is provided by the user of the implantable device application component 502. For example, the user can select the implantable device and the vibration activity from a menu populated with information based on a user's user account associated with the implantable device application component 502. In another example, the user can select a particular implantable device and/or a type of communication desired and the associated vibration activity can be automatically recalled by the implantable device authentication component 508 based on information included in the user account. In another example, the user can retrieve stored information from memory 518 of the external device 116. In yet another example, the user can manually input the information into the external device 116.

In response to the request, vibration component 510 is configured to direct the vibrator 522 of the external device 116 to perform the vibration activity. For example, the vibration component 510 can command the vibrator to physically vibrate the external device 116 in accordance with a specific vibration pattern defined by the vibration activity. When the external device 116 is located within a defined proximity to the implantable device 104 and/or touching the body of the person (or object) in which the implantable device 104 is implanted, the implantable device 104 can detect the vibration activity in accordance with one or more embodiments described herein. The implantable device 104 can then initiate, conduct or otherwise approve/enable a telemetry session with the external device 116 (or another device, such as a tertiary device 402) in response to a determination that the vibration activity corresponds, or substantially corresponds, to a vibration pattern identifier known to or otherwise able to be determined by the implantable device 104.

For example, the implantable device 104 can send an acknowledgement communication to the external device 116 (or another device, such as a tertiary device 402) indicating that the implantable device 104 has authorized the requested telemetry session. The communication component 512 is configured to receive this acknowledgment and/or facilitate communication between the external device 116 (or another device, such as tertiary device 402) and the implantable device 104 as authorized for the telemetry session.

In some embodiments, in response to reception of the acknowledgment communication, the implantable device authentication component 508 and/or the communication component 512 can establish the authorized telemetry session by facilitating the exchange of security information between the implantable device 104 and the external device 116 (e.g., based on the determination that the first vibration activity corresponds to the first vibration pattern identifier). For example, the communication component 512 can facilitate the exchange of authentication information (e.g., device identifiers for the external device 116 and the implantable device 104) and/or session keys in accordance with suitable existing pairing technology. In an embodiment, the session keys can be set to expire after a defined duration of time.

In various embodiments, communication component 512 facilitates communication between external device 116 and another device (e.g., implantable device 104, server device 404 and/or tertiary device 402). For example, communication component 512 can provide various hardware and software components associated with establishing and conducting a telemetry session between external device 116 and an implantable device 104. Although communication component 512 is depicted as part of the implantable device application component 502, it should be appreciated that one or more of the structure, features and/or functionalities of communication component 512 can be native to the external device 116. Communication component 512 can communicate with another device using various wireless communication protocols.

Server authentication component 514 is configured to facilitate authenticating and authorizing a user in association with providing the user access to the various features and functionalities of implantable device application component 502, including at least features associated with establishing an authorized telemetry session with the implantable device 104. For example, server authentication component 514 can control access to a personal user account associated with the implantable device application component 502 and server device 404 by implementing an authentication/authorization procedure (e.g., enter user name and password) prior to allowing access to the personal user account. As discussed above, the personal user account can include information identifying the user's implantable device and the vibration activity associated with accessing the implantable device. In another example, server authentication component 514 can restrict access to the vibration authentication capabilities of the implantable device application component 502 based on authentication/authorization of the user of the application with the server (e.g., via a sign in procedure).

Update/programming component 516 is configured to facilitate updating or changing the vibration activity and/or associated vibration pattern identifier combination that is used to authorize a telemetry session between an implantable device 104 and external device 116 (or a particular authorized user of the external device). In particular, as discussed supra, in some embodiments, information defining the specific vibration pattern activity to be employed by the external device 116 to establish an authorized telemetry session with the implantable device 104 can be included with the external device 116 and/or implantable device application component 502 (e.g., in memory 518) and configured to remain unchanged over time. In this embodiment, the implantable device 104 can also be programmed (e.g., prior to implantation) with the vibration pattern identifier corresponding to the specific vibration activity and the vibration pattern identifier can also be configured to remain unchanged over time. In other embodiments, the vibration activity and corresponding vibration pattern identifier associated with authorizing a telemetry session between the external device 116 and the implantable device 104 can be programmed and re-programmed by the update/programming component 516 and/or the server device after the implantable device 104 has been implanted. For example, the vibration pattern identifier can be downloaded by connection of the external device 116 to an online system after the user/external device 116 has been authenticated/registered via the implantable device application component 502.

There can be various reasons for updating or changing secret data required for access to a device or system, such as the vibration activity and associated vibration pattern identifier combination of the subject systems. For example, users of various web-based services often regularly change passwords required to access the web-based services to maintain and/or ensure the integrity of the authentication/authorization procedure. In another example, system servers often change access information for a user when the user forgets or loses the access information.

In some embodiments, update/programming component 516 can facilitate programming and re-programming or updating the information that dictates the vibration activity of the external device 116 and/or associated vibration pattern identifier that is used to authorize a telemetry session, between an implantable device 104 and external device 116, by relaying information between the implantable device 104 and the server device 404.

Figure 6:
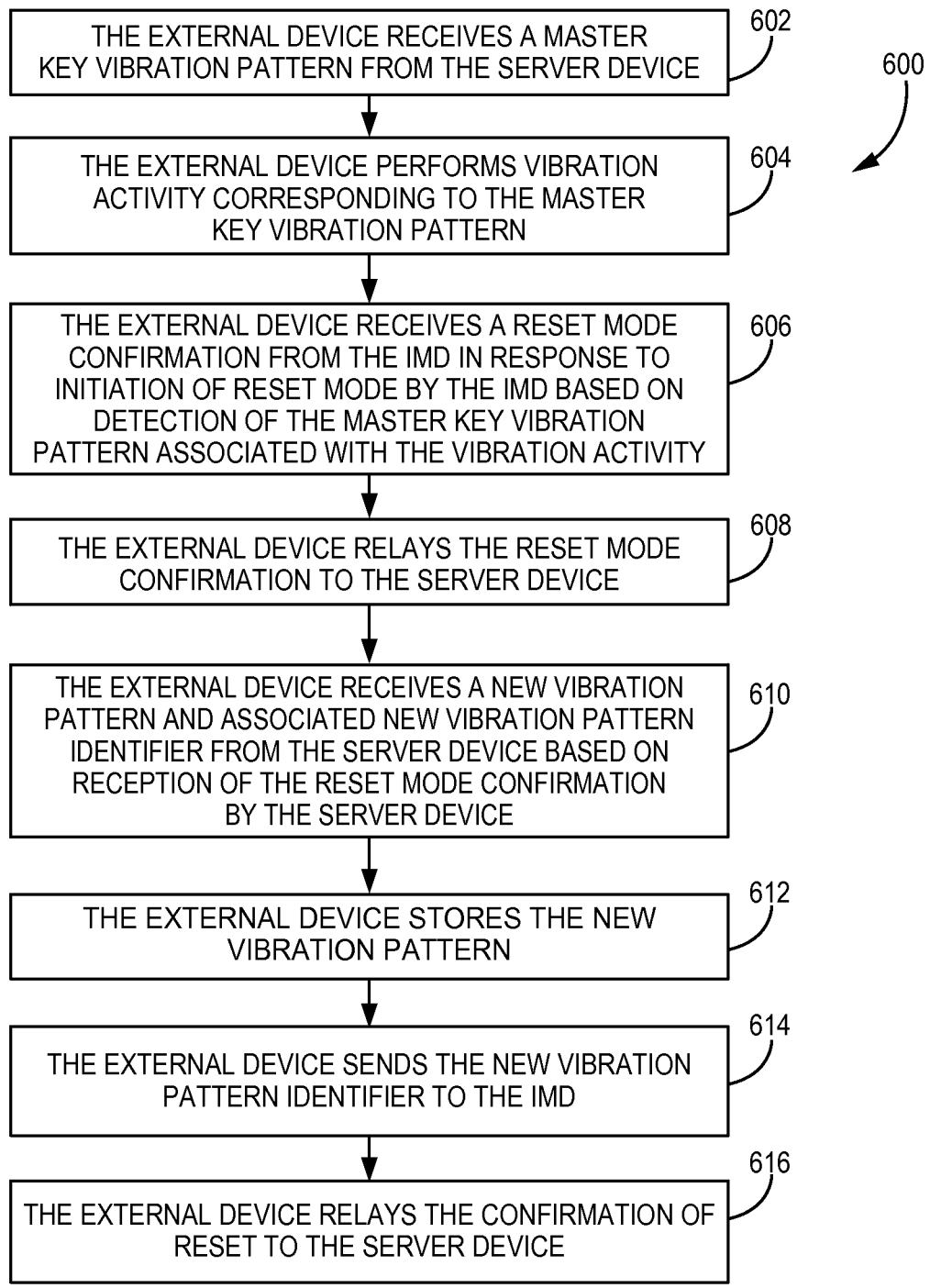
FIG. 6 illustrates a flow diagram of an example, non-limiting method to reset vibration authorization information facilitating telemetry with an implantable device in accordance with one or more embodiments described herein.

FIG. 6 illustrates a flow diagram of an example, non-limiting method to reset vibration authorization information facilitating telemetry with an implantable device in accordance with one or more embodiments described herein. Method 600 involves updating or changing the vibration activity and associated vibration pattern identifier combination that is used to authorize a telemetry session between an implantable device 104 (e.g., an IMD) and an external device 116. Method 600 is described from the perspective of an external device 116. In an embodiment, the various actions or events performed at the external device 116 in association with method 600 can be facilitated by update/programming component 516. As described supra, some embodiments, a vibration pattern identifier can be pre-stored in the external device 116 and/or the implantable device 104 prior to use of the external device 116 and prior to implantation of the implantable device 104. In other embodiments, information indicative of a changed or new vibration pattern identifier can be received and/or utilized by the external device 116 from time to time.

Now turning to FIGS. 1, 4, 5 and/or 6, at 602, the external device 116 receives information indicative of a master key vibration pattern from the server device 404. For example, update/programming component 516 can send a request to the server device 404 requesting information indicative of the vibration activity and associated vibration pattern identifier combination for a particular implantable device 104 (e.g., a particular IMD) be changed or reset.

In response to receipt of the request, the server device 404 can verify that the external device 116 and/or the user of the external device 116 is authorized to access the implantable device 104. After a determination that the external device 116 and/or the user of the external device 116 is authorized to access the implantable device 104, the server device 404 can transmit to the update/programming component 516 master data that defines a master key vibration pattern. For example, in one embodiment, the server device 404 can transmit information and/or a script that describes or otherwise identifies the master key vibration pattern. The update/programming component 516 can be configured to identify this master data as corresponding to the master key vibration pattern. In an embodiment, the master data is protected from being accessed and/or retained by the user of the external device 116 and/or the external device (e.g., via encryption).

At 602, the external device 116 performs vibration activity corresponding to the master key vibration pattern. For example, in response to reception of the master data, the update/programming component 516 and/or the vibration component 510 can direct the vibrator 522 to perform master key vibration activity corresponding to the master key vibration pattern. The update/programming component 516 can be configured to receive the master data and cause the external device 116 to vibrate based on the master data automatically and without user intervention/input in some embodiments.

At 604, the external device 116 receives a reset mode confirmation from the IMD in response to initiation of reset mode by the IMD based on detection of the master key vibration pattern associated with the vibration activity. For example, the IMD can sense and interpret the master key vibration activity in a manner similar to any other vibration activity. In response to a determination that the master key vibration activity corresponds to a master key vibration pattern identifier known to the IMD, the IMD can enter reset mode. The IMD can then send a reset mode confirmation message to the external device 116.

At 608, the external device relays the reset mode confirmation to the server device 404. For example, update/programming component 516 can automatically (e.g., without user intervention or input) send the reset mode confirmation to the server device 404 via a network. In another embodiment, the IMD can be configured to send the reset mode confirmation directly to the server device 404 via a network.

At 610, the external device 116 receives a new vibration pattern and associated vibration pattern identifier from the server device 404 based on reception of the reset mode confirmation from the server device 404. For example, the external device 116 can receive data that resembles a script defining the new vibration pattern and the associated vibration pattern identifier for the new vibration pattern. At 612, the external device 116 stores the new vibration pattern. For example, the external device 116 can store the data that resembles the script defining the new vibration pattern under a name identifiable to the user (e.g., "New Vibration Pattern_2015," or "Erin's IMD Vibration Pattern").

At 614, the external device 116 sends the new vibration pattern identifier to the IMD. In some embodiments, the IMD closes the reset mode and sends confirmation of reset of the vibration pattern identifier to the external device 116 upon receipt of the new vibration pattern identifier. In another embodiment, the server device 404 can communicate the new vibration pattern identifier directly to the IMD via a network.

At 616, the external device 116 relays the confirmation reset to the server device 404. In response to reception of the reset confirmation, the server device 404 can update client/user records with the new vibration pattern.

In another embodiment, (not shown), after step 608 (and instead of steps 610-616), the server device 404 can relay the new vibration pattern identifier to the IMD, either directly via a network or using external device 116 as a relay. In response to reception of the new vibration pattern identifier by the IMD, the IMD can store the new vibration pattern identifier in memory (e.g., and erase an old vibration pattern identifier). The IMD can then close reset mode and send confirmation of the reset to the server device 404, either directly or using the external device 116 as a relay. In response to reception of the reset confirmation, the server device 404 can update the user's account with the new vibration pattern. The new vibration pattern can then be accessed by the external device 116 (or by the user of the external device 116) via the user's user account (e.g., after the user signs in to the user account in accordance with embodiments described herein).

The external device 116, implantable device 104 and server device 404 (e.g., system 400) can employ a same or similar method as reset method 600 to facilitate initial programming of the external device 116 and the implantable device with a vibration activity/vibration pattern identifier pair. For example, at initial programming, after the user of external device 116 and/or the external device has been authenticated by the remote server device 404 as being authorized to employ the implantable device application component 502 (e.g., because the user/external device 116 have registered for a user account and the identity of the user/external device has been verified), the external device 116 (e.g., via update/programming component 516) can request assignment of a unique vibration activity and corresponding vibration pattern identifier to the user/external device 116 and the implantable device 104, respectively. The external device 116 can send this initial programming request to the server device 404. In response to receipt of the request, the server device 404 can verify that the external device 116 and/or the user of the external device 116 is authorized to access the implantable device 104. After a determination that the external device 116 and/or the user of the external device 116 is authorized to access the implantable device 104, the server device 404 can transmit, to the external device 116, master data that defines a master key vibration pattern, as discussed above.

The external device 116 can then perform the vibration activity corresponding to the master key vibration pattern. In response to performance of the master key vibration pattern, the external device 116 can receive a programming mode confirmation from the IMD in response to initiation of programming mode by the IMD based on detection of the master key vibration pattern associated with the vibration activity. For example, the IMD can sense and interpret the master key vibration activity in a manner similar to any other vibration activity. In response to a determination that the master key vibration activity corresponds to a master key vibration pattern identifier known to the IMD, and in response to a determination that a unique vibration pattern identifier associated with access of the IMD by a specific external device (e.g., external device 116) has not yet been assigned to the IMD, the IMD can enter programming mode (as opposed to reset mode).

Similar to the reset mode process 600, the IMD can send a programming mode confirmation message to the external device 116. The external device can further relay the programming mode confirmation to the server device 404 (e.g., similar to the reset mode confirmation). The external device 116 then receives or accesses, (e.g., via the user account), an initial vibration pattern and associated initial vibration pattern identifier from the server device 404 based on reception of the programming mode confirmation by the server device 404 (e.g., similar to the new vibration pattern activity/identifier associated with reset). For example, the external device can store information received from the server device 404 defining the initial vibration activity in memory 518. In another example, information defining the initial vibration activity can be assigned to the user account for the user/external device 116 and later retrieved via accessing the user account (e.g., via a connection to the server device 404 via a network after logging in).

In some embodiment, the external device 116 can further send the corresponding initial vibration pattern identifier received by the external device 116 from the server device 404 to the IMD. In an embodiment, upon reception of the initial vibration pattern identifier, the IMD stores the initial vibration pattern in memory of the IMD, closes programming mode, and sends confirmation of initial programming to the external device 116. The external device 116 can further relay the initial programming confirmation to the server device 404. In response to reception of the initial programming confirmation, the server device 404 can update client/user records with the initial vibration pattern.

Humans are incapable of practicing all of the steps of method 600, and therefore, ipso facto, the various aspects of method 600 cannot be mere implementations of well-known or fundamental economic or human behavior nor as disembodied, mental or abstract steps or embodiments. For example, the method 600 involves the performance of vibration activity by a device corresponding to a master key vibration pattern. As discussed infra, such vibration activity involves using various electrical and mechanical components and circuitry configured to generate vibration activity corresponding to highly specific vibration patterns with intricate variations in vibration displacement, velocity, acceleration, time period and/or frequency. Humans are incapable of replicating such vibration activity without the use of complex machines. In another example, several aspects of method 600 involve the wireless transmission/reception of data over a wireless network, an action humans cannot perform.

Figure 7:
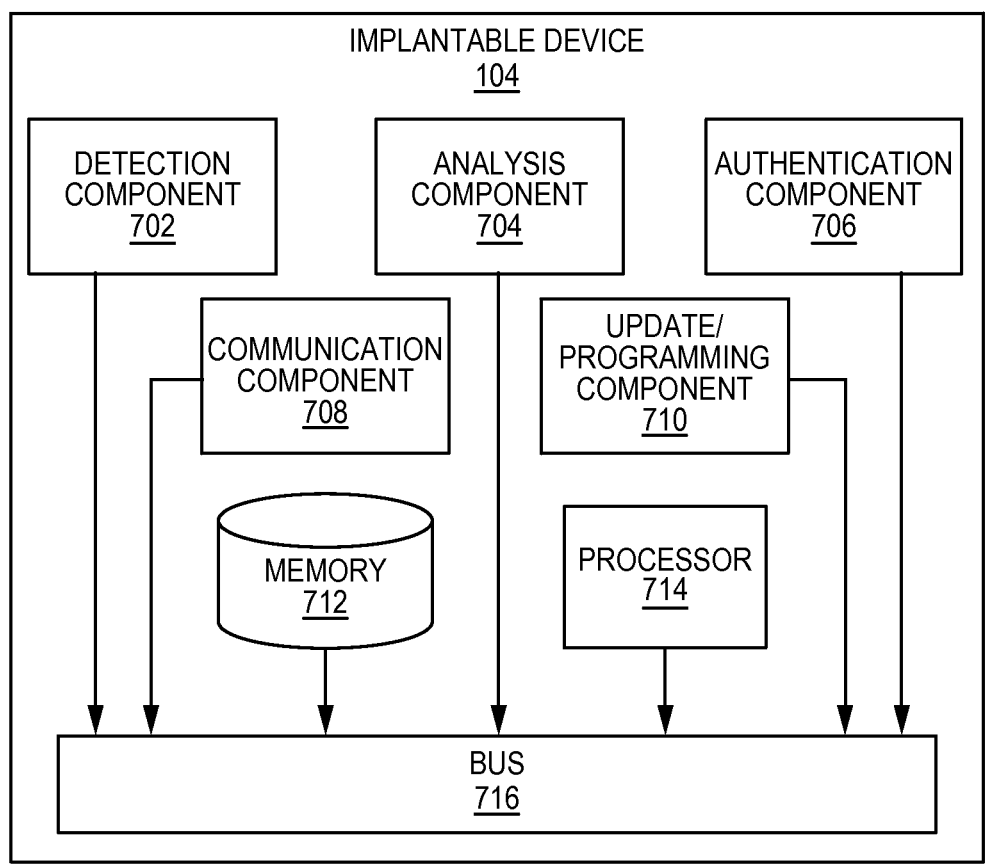
FIG. 7 illustrates a block diagram of an example, non-limiting implantable device configured to employ a vibration-based authentication process to facilitate establishing a telemetry session with an external device in accordance with one or more embodiments described herein.

FIG. 7 illustrates a block diagram of an example, non-limiting implantable device configured to employ a vibration-based authentication process to facilitate establishing a telemetry session with an external device in accordance with one or more embodiments described herein. Repetitive description of like elements employed in other embodiments described herein is omitted for sake of brevity.

As shown, an example implantable device 104 can include a detection component 702, an analysis component 704, an authentication component 706, a communication component 708 and/or an update/programming component 710. The implantable device 104 can also include memory 712 that stores computer executable components, and a processor 714 that executes the computer executable components stored in the memory 712. Implantable device 104 can include a bus 716 that couples the various components of the implantable device 104, including, but not limited to, detection component 702, analysis component 704, authentication component 706, communication component 708, update/programming component 710, memory 712, and a processor 714.

In some embodiments, one or more of aspects of the detection component 702, analysis component 704, authentication component 706, communication component 708 and/or update/programming component 710 can be employed as hardware or circuitry (e.g., detection component 702 can be or include a piezoelectric sensor, accelerometer or the like), software or a combination of hardware and software. In some embodiments, one or more of the detection component 702, analysis component 704, authentication component 706, communication component 708 and/or update/programming component 710 can be embodied as or include computer executable components.

With reference to FIGS. 1 and 4, communication component 708 is configured to facilitate communication between the implantable device 104 and another device (e.g., external device 116, server device 404 and/or tertiary device 402). Communication component 708 can include one or more of the structure, features and functionalities as communication component 512. For example, communication component 708 can include a transmitter and/or receiver configured to transmit and/or receive electrical wireless signals. As another example, communication component 708 can be configured to communicate with another device using various wireless communication protocols, including but not limited to: NFC, BLUETOOTH® technology, RF communications, SIP-based communications, cellular communication, or other forms of communication including both proprietary and non-proprietary communication protocols.

Detection component 702 is configured to detect or sense vibration activity using one or more vibration sensors or circuitry within or electrically (or mechanically) coupled to the implantable device 104. These sensors can include, but are not limited to, an accelerometer and/or a piezoelectric sensor (e.g., a piezoelectric displacement sensor, a piezoelectric velocity sensor, a piezoelectric pressure sensor, etc.). In an embodiment, the detection component 702 includes circuitry with the one or more vibration sensors.

The detection component 702 can be further configured to generate vibration data output corresponding to detected vibration parameters of the vibration activity. In various embodiments, the vibration data output can be generated by circuitry designed to output specific types of information or electrical signals and/or based on changes in mechanical, electrical or electromechanical features or components of one or more devices or circuits that can be included in the detection component 702. In some embodiments, the detection component 702 can generate the vibration data based on one or more operations of computer executable components of the implantable device 104.

As discussed supra, these parameters can vary depending on the sensor or sensors employed by the detection component 702, but can include velocity, acceleration, displacement, intensity and/or duration measurements. Detection component 702 can include or employ a clock to determine a time component (e.g., the duration of the vibration activity within a vibration pattern and/or the duration of the entirety of the vibration pattern). In some embodiments, the vibration data output can chart and/or otherwise determine the one or more of the detected parameters as a function of time.

Analysis component 704 is configured to analyze the vibration data output of the detection component 702 to determine and/or identify a vibration pattern in the vibration data. In an embodiment, in order to determine and/or identify the vibration pattern, the analysis component 704 can identify and/or classify one or more vibration behaviors included in the vibration data. As discussed supra, these vibration behaviors can include, but are not limited to, the vibration on activity, the vibration off activity, the duration or sequence of vibration on and vibration off activities, successive and different durations of vibration on and vibration off patterns, a time period associated with a sequence of two or more vibrations, intensity of vibrations and/or the intensity variation between a sequence of two or more vibrations.

The analysis component 704 can chart and/or otherwise determine or evaluate these vibration behaviors based on the time component associated with the respective vibration behaviors to determine a pattern represented by the vibration behaviors. In one embodiment, this pattern can take the form of a vibration pattern script that charts and/or provides information descriptive of the one or more vibration behaviors as a function of time. In some embodiments, the analysis component 704 can generate a condensed digital summary of the vibration pattern script by selecting a few unique interest points in the data and generating a vibration pattern fingerprint that uniquely corresponds to the vibration pattern script. One example, of a vibration pattern script can include a complex sequence of overlapping vibration behaviors. For instance, the duration of a vibration pattern can be divided into a sequence of time segments or windows. Each segment can include one or more vibration behavior components, including but not limited to, a frequency variation of the vibration, an on/off pattern of the vibration, a displacement of the vibration, a velocity of the vibration and/or an acceleration variation of the vibration. For example, each of these different vibration pattern components can be evaluated and/or charted individually as a function of time and then grouped together by association with a same time segment.

Analysis component 704 is further configured to compare the determined vibration pattern (e.g., the vibration pattern script) or the vibration pattern fingerprint with one or more vibration pattern identifiers stored in memory 712 to determine whether the determined vibration pattern or vibration pattern fingerprint corresponds to a vibration pattern identifier stored in the memory 712. For example, the vibration pattern identifiers can be associated with information defining reference vibration patterns (e.g., reference vibration pattern scripts) or the vibration pattern fingerprint identifiers can include reference vibration pattern fingerprints. In some embodiments, the analysis component 704 and/or the implantable device 104 generally can compare the vibration pattern (or the vibration pattern fingerprint) with information accessible by the analysis component 704 or the implantable device 104 via access of the communication component 708 to a repository of information that can be retrieved and/or accessed over a network to which the implantable device 104 can be communicatively coupled.

Analysis component 704 can compare a determined vibration pattern or fingerprint with a vibration pattern identifier or vibration pattern fingerprint identifier to determine a degree of correspondence or similarity (e.g., 100% match, 95% match, 75% match, etc.) between a determined vibration pattern or vibration pattern fingerprint and a vibration pattern identifier or vibration pattern fingerprint identifier.

Analysis component 704 can characterize a determined vibration pattern or determined vibration pattern fingerprint as a valid match with a vibration pattern identifier or vibration pattern fingerprint identifier based on a threshold correspondence degree requirement. For example, if a determined vibration pattern exhibits a degree of similarity to a vibration pattern identifier above a defined threshold (e.g., 100% match, 95% match, 75% match), the analysis component 704 can characterize the determined vibration pattern as a valid match. If a determined vibration pattern exhibits a degree of similarity to a vibration pattern identifier below the threshold requirement (e.g., 20% match, 35% match, 60% match, etc.), the analysis component 704 can characterize the determined vibration pattern as an invalid match.

In another embodiment the implantable device 104 can include one or more vibration sensors and/or circuitry that are sensitive to certain vibrations. For example, a sensor and circuitry can be configured to generate a positive output value in response to detection of specific combination of vibration displacement, velocity, acceleration, or frequency parameters. The positive output value can indicate the detected vibration activity corresponds to a correct vibration pattern associated with authorized access to the implantable device 104 by the external device 116. In the absence of detection of the specific combination of vibration measurement parameters, a sensor and or circuitry can merely continue sensing. According to this embodiment, the vibration sensors and circuitry can send an electrical signal directly to the authorization component 706 and/or communication component 708 indicative of the positive output value. In response to reception of the electrical signal, the authorization component 706 can automatically authorize the telemetry session and the communication component 708 can initiate the telemetry session (or, in some cases, continue an ongoing telemetry session).

Authentication component 706 can be configured to authorize a telemetry session between the implantable device 104 and the external device 116 (or a tertiary device 402) based on a determination that a detected vibration pattern is a valid match (e.g., has an acceptable degree of similarity) with a vibration pattern identifier (or, as described, based on a determination that the detected vibration pattern has caused one or more behaviors or signals to be generated in a detection circuit or an analysis circuit of the implantable device 104, that indicates a desired particular vibration pattern has been detected). In some embodiments, authentication component 706 can direct communication component 708 to begin communicating with the external device in accordance with the parameters of the authorized telemetry session.

In an embodiment, the authentication component 706 is configured to generate an acknowledgment message that can communicated to the external device 116 that informs the external device 116 that the requested telemetry session has been authorized. The communication component 708 can send the acknowledgment message to the external device 116. In some embodiments, the authentication component 706 and/or the communication component 708 can perform one or more steps to establish the authorized telemetry session by also facilitating the exchange of security information between the implantable device 104 and the external device 116. For example, the communication component 708 can facilitate the exchange of authentication information (e.g., device identifiers for the external device 116 and the implantable device 104) and/or session keys in accordance with suitable existing pairing technology. In one embodiment, the session keys can be configured to expire after a defined duration of time has elapsed after the pairing process has been initiated.

In an embodiment, the vibration pattern identifiers can be associated with information defining the parameters/type of communications authorized for the telemetry session. For example, a vibration pattern identifier can be associated with information indicating that the external device 116 is only authorized to read data from the implantable device 104. In another example, a vibration pattern identifier can be associated with information indicating that the external device 116 is authorized to read data from the implantable device 104 and transmit commands to the implantable device 104 to cause programming of the implantable device 104 or another implanted device associated with the implantable device 104 (e.g., programming mode). According to this embodiment, communication component 708 can communicate with the external device 116 in accordance with the type of communications authorized for the telemetry session. In another embodiment, a vibration pattern identifier can be associated with information defining a tertiary device (e.g., tertiary device 402) with which to establish the telemetry session. This embodiment employs vibration from the external device 116 to establish telemetry with a tertiary device (e.g., tertiary device 402). According to this embodiment, communication component 708 can communicate with the tertiary device (e.g., tertiary device 402) in accordance with the type of communications authorized for the telemetry session.

Update/programming component 710 is configured to facilitate re-programming of the implantable device 104 by the external device 116 (or a tertiary device 402 with which the implantable device 104 has an authorized telemetry session) or updating the vibration activity and associated vibration pattern identifier combination that is used to authorize a telemetry session between implantable device 104 and external device 116 (or the tertiary device 402, depending on the embodiment as described above). In some embodiments, one or more of the various actions or events performed at the implantable device 104 described in association with method 600 are facilitated or performed by update/programming component 710.

Figure 8:
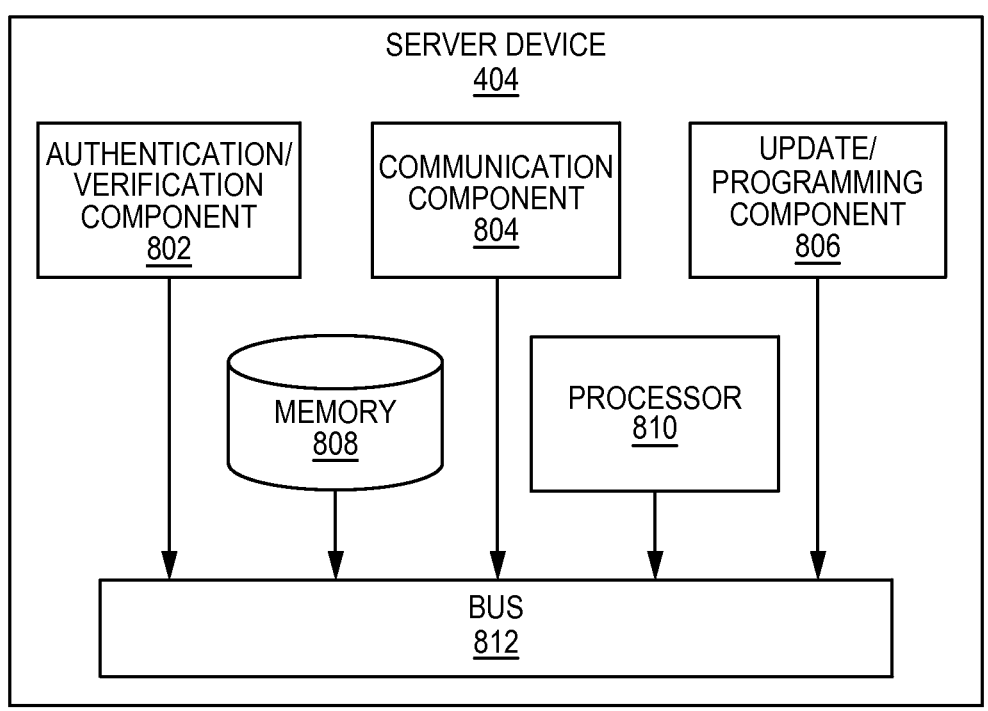
FIG. 8 illustrates a block diagram of an example, non-limiting server device configured to facilitate a vibration-based authentication process between an external device and an implantable device for establishment of a telemetry session between the external device and the implantable device in accordance with one or more embodiments described herein.

FIG. 8 illustrates a block diagram of an example, non-limiting server device configured to facilitate a vibration-based authentication process between an external device and an implantable device for establishment of a telemetry session between the external device and the implantable device in accordance with one or more embodiments described herein. Repetitive description of like elements employed in other embodiments described herein is omitted for sake of brevity.

Example server device 404 can include an authentication/verification component 802, a communication component 804, and an update/programming component 806. Server device 404 can also include memory 808 that stores computer executable components, and a processor 810 that executes computer executable components stored in the memory 808, (e.g., one or more of the authentication/verification component 802, communication component 604, and update/programming component 806.). Server device 404 can include a bus 812 that couples the various components of the server device 404, including, but not limited to, authentication/verification component 802, communication component 804, update/programming component 806, memory 808, and a processor 810.

Communication component 804 is configured to facilitate communication between the server device 404 and another device (e.g., external device 116, implantable device 104 and/or tertiary device 402). Communication component 804 can include one or more of the features and functionalities as communication component 512. For example, communication component 512 can include a transmitter and/or receiver configured to transmit and/or receive electrical wireless signals. For example, communication component 804 can communicate with another device using various wireless communication protocols including, but not limited to, RF communications or other forms of communication including both proprietary and non-proprietary communication protocols.

In an embodiment, server device 404 is configured to facilitate operations of an application (e.g., implantable device application component 502) provided on the external device 116 that is used by the external device 116 to interact with the implantable device 104. For example, the server device 404 can provide different users a variety of services associated with the implantable device application component 502 for the external device with which a particular user is associated. For instance, when the implantable device is an IMD, one of these services can include retaining and/or providing access to patient health information/records associated with the IMD of the patient. Another of these services can include managing different levels of access to the IMD by different users (or by different external devices associated by different users). In association with managing access to the IMD by different users, the server device 404 can access one or more different accounts or repositories of information associated with the different users.

Authentication/verification component 802 is configured to facilitate authenticating/verifying a user and/or a device in association with accessing a user account hosted by or accessed by the server device 404. Authentication/verification component 802 can facilitate verifying the identity of a user (or of an external device associated with user) in association with access of the user's account using a secure sign in procedure. Authentication/verification component 802 can employ various user authentication/authorization protocols to perform the secure sign in procedure. For example, authentication/verification component can employ a username and password system, an external authorization system, a single sign-on service and/or a PKI system. In an embodiment, the authentication/verification component 802 can utilize user sign in information provided to the server device 404 to access a particular user account and/or their personal information associated with the user account. The authentication/verification component 802 can also determine whether the sign in has been successfully performed prior to allowing the user (or external device associated with the user) to access the vibration-based authorization functionality provided by the application on a client device (e.g., implantable device application component 502).

Update/programming component 806 is configured to facilitate re-programming or updating the vibration activity and associated vibration pattern identifier combination that is used to authorize a telemetry session between the implantable device 104 and external device 116 (or another device). In some embodiments, one or more of the various actions or events performed at the server device 404 described in association with method 600 can be facilitated and/or performed by update/programming component 806.

Figure 9:
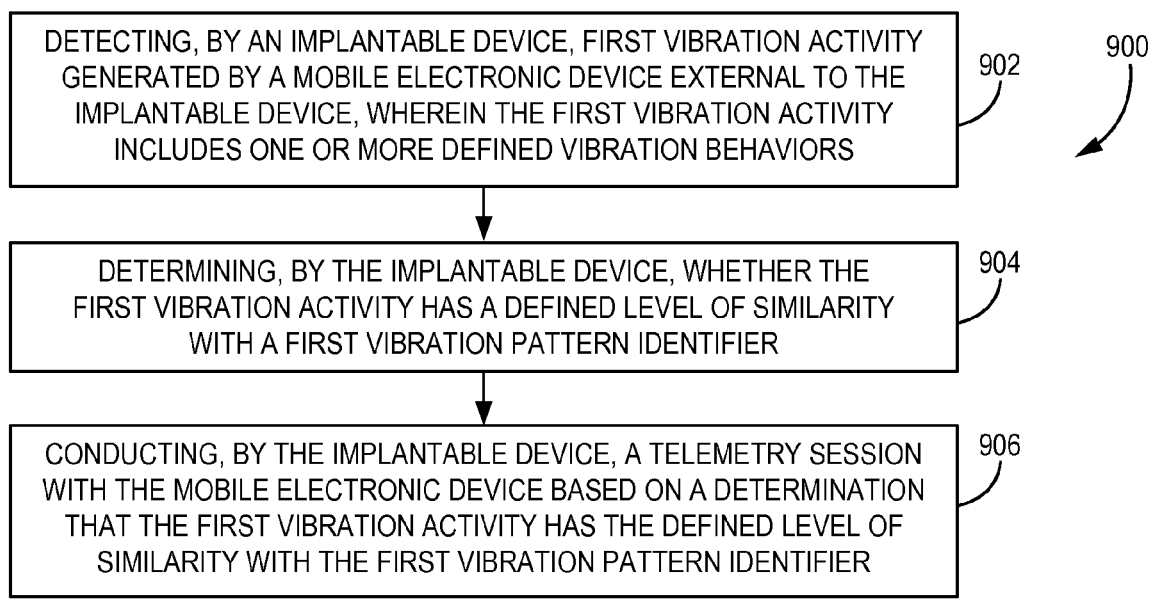
FIG. 9 illustrates a flow diagram of an example, non-limiting method facilitating telemetry with an implantable device based on vibration of an external device in accordance with one or more embodiments described herein.
Figure 10:
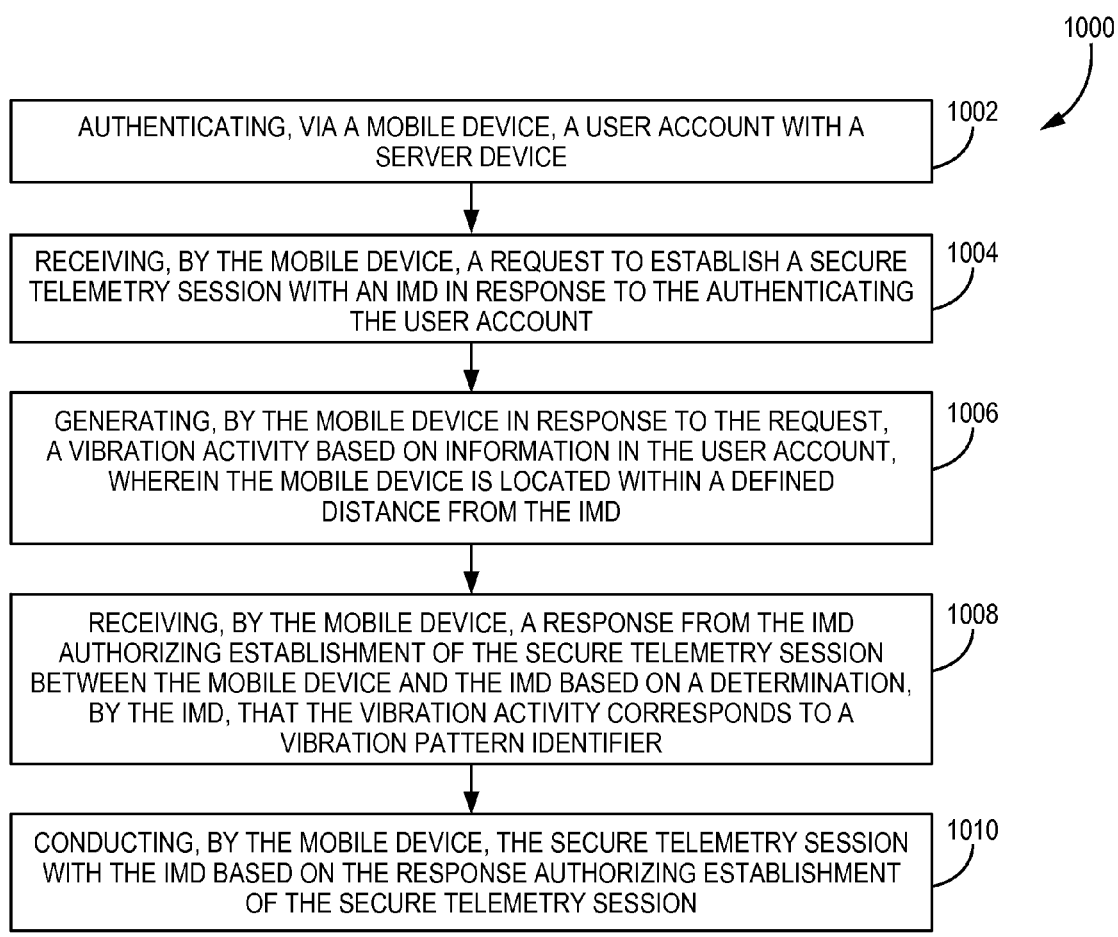
FIG. 10 illustrates a flow diagram of another example, non-limiting method facilitating telemetry with an implantable device based on vibration of an external device in accordance with one or more embodiments described herein.

In view of the example systems and/or devices described herein, example methods that can be implemented in accordance with the disclosed embodiments can be further appreciated with reference to flowcharts in FIGS. 9 and 10. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and/or described herein. For example, a method disclosed herein can alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification. It should be further appreciated that the methods disclosed throughout the subject specification are configured to being stored on an article of manufacture to facilitate transporting and transferring such methods to computers for execution by a processor or for storage in a memory.

FIG. 9 illustrates a flow diagram of an example, non-limiting method facilitating telemetry with an implantable device based on vibration of an external device in accordance with one or more embodiments described herein. Repetitive description of like elements employed in other embodiments described herein is omitted for sake of brevity.

With reference to FIGS. 1 and 9, at 902, an implantable device detects a first vibration activity generated by a mobile electronic device (e.g., external device 116) external to the implantable device 104, wherein the first vibration activity includes one or more defined vibration behaviors. For example, implantable device 104 can detect vibration activity of an external device 116, such as a mobile telephone or other mobile device, in response to vibration of the external device 116 when the external device 116 is placed within proximity to the implantable device 116. When the implantable device 116 is or includes an IMD that is worn by a patient, the external device 116 can be pressed against the body of the patient at a location within a distance of the implantable device 104 at which the vibration can be detected by the implantable device 104.

At 904, the implantable device determines whether the first vibration activity has a defined level of similarity with a first vibration pattern identifier (e.g., stored in memory of the implantable device 104). At 906, the implantable device 104 conducts a telemetry session with the mobile electronic device based on a determination that the first vibration activity has the defined level of similarity with the first vibration pattern identifier.

FIG. 10 illustrates a flow diagram of another example, non-limiting method facilitating telemetry with an implantable device based on vibration of an external device in accordance with one or more embodiments described herein. Repetitive description of like elements employed in other embodiments described herein is omitted for sake of brevity.

With reference to FIGS. 1, 4 and 10, at 1002, a mobile device (e.g., external device 116) authenticates a user account with a server device (e.g., server device 404). For example, a user associated with the mobile device can have an account with an IMD management system that employs a client application and an application service provider (e.g., at a server device) to render various services to the entities. The mobile device can include the client application. In order to establish a session with the application service provider, the user associated with the mobile device can connect to the application service provider server device via a network, open the application on the mobile device, and login to the user account by providing security information (e.g., a username and password). The application service provider can then perform an authentication/authorization method to determine whether the user (or mobile device associated with the user) is authorized to access the user account. In response to a determination that the user is authorized, the application service provider can provide the user access to his or her user account via the client application on the mobile device.

At 1004, the mobile device receives a request to establish a secure telemetry session with an IMD in response to the authenticating the user account at 1002. For example, after the user has logged in to his or her user account, the user (or mobile device associated with the user) can employ a functionality of the client application that allows the user (or mobile device associated with the user) to access vibration security information required to access the IMD (e.g., vibration pattern activity identifiers and their corresponding vibration pattern script), and/or that allows the user to control the vibration activity of the mobile device in accordance with the vibration security information. For instance, the vibration security information can identify an IMD and the associated vibration pattern/activity required to access the IMD. Via the application, the user (or mobile device associated with the user) can select the IMD and indicate the vibration pattern/activity that should be used to authenticate the telemetry session between the mobile device and the IMD. In an embodiment, the particular vibration pattern/activity can be associated with an identifier for the IMD such that, in response to selection of information identifying the IMD, the correct vibration pattern/activity is automatically retrieved by the application and included in the request to the IMD to establish the telemetry session. In another embodiment, information indicating a selection of the correct vibration pattern/activity can be provided via selection of an option at an electronic menu of options.

At 1006, the mobile device generates the vibration activity in response to the request based on information in the user account (e.g., the information defining the vibration pattern script corresponding to the vibration activity). The mobile device can be located within a defined distance from the IMD when the mobile device vibrates so that the vibrations can be detected by the IMD. At 1008, the mobile device receives a response from the IMD authorizing establishment of a secure telemetry session between the mobile device and the IMD based on a determination, by the IMD, that the vibration activity corresponds to a vibration pattern identifier (known to the IMD). At 1010, the mobile device then conducts the secure telemetry session with the IMD based on the response authorizing establishment of the secure telemetry session.

Figure 11:
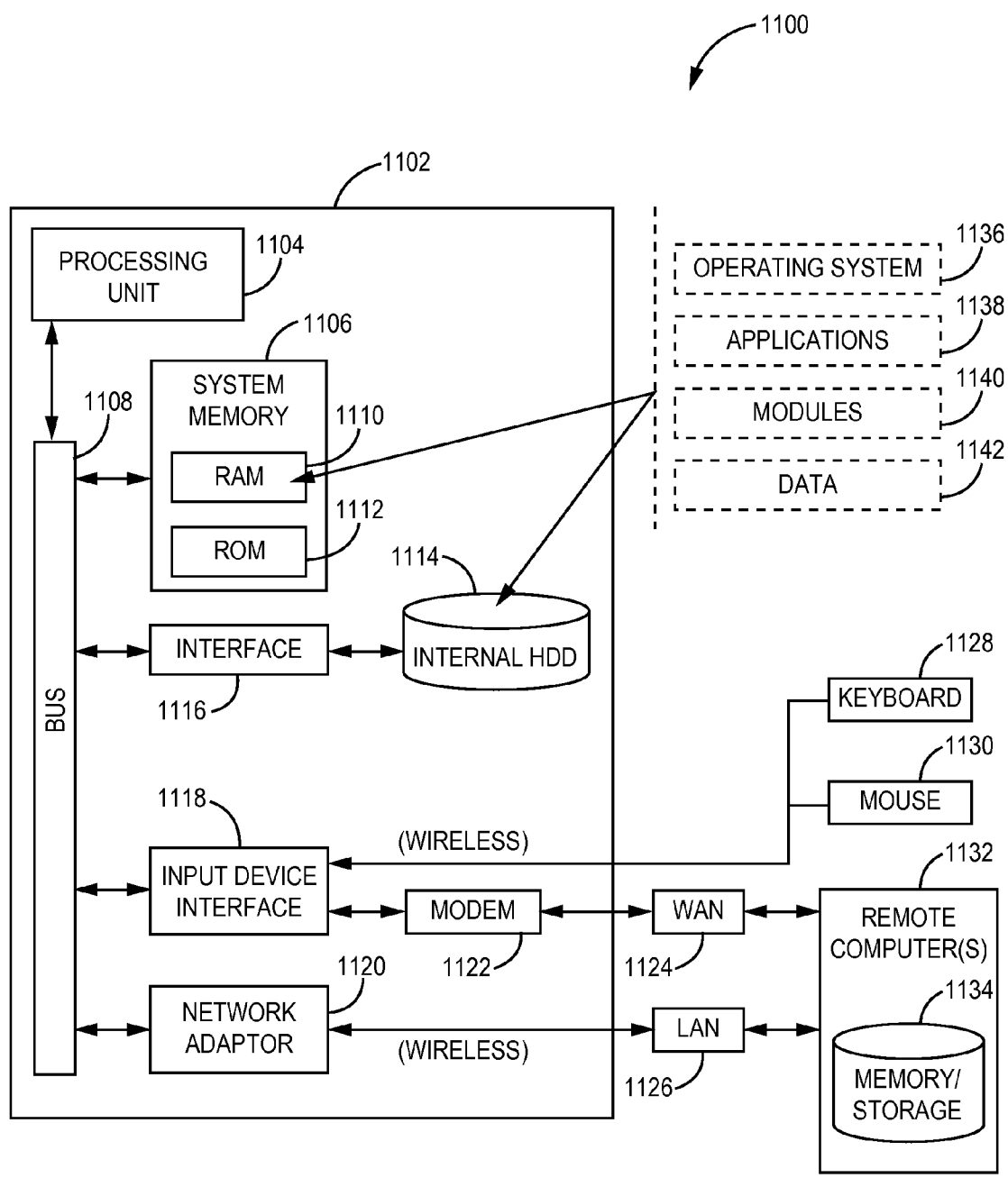
FIG. 11 illustrates a block diagram of a computer operable to facilitate telemetry with an implantable device based on vibration of an external device in accordance with one or more embodiments described herein.

FIG. 11 illustrates a block diagram of a computer operable to facilitate telemetry with an implantable device based on vibration of an external device in accordance with one or more embodiments described herein. For example, in some embodiments, the computer can be or be included within implantable device 104, external device 116, tertiary device 402, and/or server device 404. Repetitive description of like elements employed in other embodiments described herein is omitted for sake of brevity.

In order to provide additional context for one or more embodiments described herein, FIG. 11 and the following discussion are intended to provide a brief, general description of a suitable computing environment 1100 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, example environment 1100 for implementing one or more embodiments of the embodiments described herein includes computer 1102, computer 1102 including processing unit 1104, system memory 1106 and system bus 1108. System bus 1108 couples system components including, but not limited to, system memory 1106 to processing unit 1104. Processing unit 1104 can be any of various commercially available processors. Dual microprocessors and other multi-processor architectures can also be employed as processing unit 1104.

System bus 1108 can be any of several types of bus structure that can further interconnect to a memory bus (with or without a memory controller), a peripheral bus, and a local bus using any of a variety of commercially available bus architectures. System memory 1106 includes RAM 1110 and ROM 1112. A basic input/output system (BIOS) can be stored in a non-volatile memory such as ROM, erasable programmable read only memory (EPROM), EEPROM, which BIOS contains the basic routines that help to transfer information between elements within computer 1102, such as during startup. RAM 1110 can also include a high-speed RAM such as static RAM for caching data.

Computer 1102 further includes internal hard disk drive (HDD) 1114 (e.g., Enhanced Integrated Drive Electronics (EIDE), Serial Advanced Technology Attachment (SATA)). HDD 1114 can be connected to system bus 1108 by hard disk drive interface 1116. The drives and their associated computer-readable storage media provide nonvolatile storage of data, data structures, computer-executable instructions, and so forth. For computer 1102, the drives and storage media accommodate the storage of any data in a suitable digital format.

A number of program modules can be stored in the drives and RAM 1110, including operating system 1136, one or more application programs 1138, other program modules 1140 and program data 1142. All or portions of the operating system, applications, modules, and/or data can also be cached in RAM 1110. The systems and methods described herein can be implemented utilizing various commercially available operating systems or combinations of operating systems.

A mobile device can enter commands and information into computer 1102 through one or more wireless input devices, e.g., wireless keyboard 1128 and a pointing device, such as wireless mouse 1130. Other input devices (not shown) can include a smart phone, tablet, laptop, wand, wearable device or the like. These and other input devices are often connected to the processing unit 1104 through input device interface 1118 that can be coupled to system bus 1108, but can be connected by other interfaces, such as a parallel port, an IEEE serial port, a game port and/or a universal serial bus (USB) port.

Computer 1102 can operate in a networked environment using logical connections via wired and/or wireless communications to one or more remote computers, such as remote computer(s) 1132. Remote computer(s) 1132 can be a workstation, a server computer, a router, a personal computer, portable computer, microprocessor-based entertainment appliance, a peer device or other common network node, and typically includes many or all of the elements described relative to computer 1102, although, for purposes of brevity, only memory/storage device 1134 is illustrated. The logical connections depicted include wired/wireless connectivity to a local area network (LAN) 1126 and/or larger networks, e.g., WAN 1124, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1102 can be connected to local network through a wired and/or wireless communication network interface or adapter 1120. Adapter 1120 can facilitate wired or wireless communication to LAN 1126, which can also include a wireless access point (AP) connected to the LAN 1126 for communicating with adapter 1120.

When used in a WAN networking environment, computer 1102 can include modem 1122 or can be connected to a communications server on WAN 1124 or has other means for establishing communications over WAN 1124, such as by way of the Internet. Modem 1122, which can be internal or external and a wired or wireless device, can be connected to system bus 1108 via input device interface 1116. In a networked environment, program modules depicted relative to computer 1102 or portions thereof, can be stored in a remote memory/storage device. It will be appreciated that the network connections shown are example and other means of establishing a communications link between the computers can be used.

Computer 1102 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 15 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, f(x)=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable device, comprising:
 a detection component configured to:
  detect first vibration activity generated by a mobile electronic device external to the implantable device, wherein the first vibration activity comprises one or more defined vibration behaviors;
 a memory that stores executable components; and
 a processor that executes at least the following executable components stored in the memory:
  an analysis component configured to determine whether the first vibration activity has a defined level of similarity with a first vibration pattern identifier; and
  a communication component configured to establish a secure telemetry session between the implantable device and the mobile electronic device based on a determination that the first vibration activity has the defined level of similarity with the first vibration pattern identifier, wherein the secure telemetry session facilitates a defined type of wireless communication session between the implantable device and the mobile electronic device, and wherein the defined type of wireless communication session is selected from a plurality of defined types of wireless communication sessions based on the first vibration pattern identifier.

2. The implantable device of claim 1, wherein the communication component is further configured to facilitate communication of security information between the implantable device and the mobile electronic device based on the determination that the first vibration activity has the defined level of similarity with the first vibration pattern identifier.

3. The implantable device of claim 1, wherein the communication component is further configured to forgo communication with the mobile electronic device based on a determination that the first vibration activity fails to have the defined level of similarity with the first vibration pattern identifier.

4. The implantable device of claim 1, wherein the detection component comprises an accelerometer configured to detect the first vibration activity.

5. The implantable device of claim 1, wherein the detection component comprises a piezoelectric sensor configured to detect the first vibration activity.

6. The implantable device of claim 1, wherein the one or more defined vibration behaviors comprises a pattern of two or more vibrations of the mobile electronic device.

7. The implantable device of claim 6, wherein the one or more defined vibration behaviors further comprises a time period associated with the pattern of two or more vibrations of the mobile electronic device.

8. The implantable device of claim 1, wherein the mobile electronic device comprises a mobile telephone.

9. The implantable device of claim 1, wherein the mobile electronic device is communicatively coupleable to, and configured to receive information from, a server device over a network, and wherein the information is indicative of the one or more defined vibration behaviors.

10. The implantable device of claim 1, wherein the mobile electronic device is communicatively coupleable to, and configured to receive information from, a server device over a network, and wherein the information is indicative of an approval by the server device to initiate the first vibration activity by the mobile electronic device based on receipt, from the mobile electronic device, of login information for a user of the mobile electronic device.

11. An implantable device, comprising:
a detection component configured to detect first vibration activity generated by an electronic device external to the implantable device, wherein the first vibration activity comprises one or more defined vibration behaviors;
an analysis component configured to determine whether the first vibration activity has a defined correlation with a first vibration pattern identifier; and
a communication component configured to facilitate a first level of wireless communication of a plurality of levels of wireless communication between the electronic device and the implantable device based on a determination that the first vibration activity has the defined correlation with the first vibration pattern identifier, wherein the first level of wireless communication is based on the first vibration pattern identifier, and based on a determination of whether the first vibration activity is a first iteration of vibration activity or a second iteration of vibration activity.

12. The implantable device of claim 11, wherein the first iteration of vibration activity and the second iteration of vibration activity are associated with different vibration behaviors.

13. The implantable device of claim 11, wherein the communication component is further configured to facilitate the first level of wireless communication between the electronic device and the implantable device a determination that the first vibration activity is the first iteration of vibration activity, and wherein the first level of wireless communication comprises initiation of a telemetry session between the implantable device and the electronic device.

14. The implantable device of claim 11, wherein the communication component is further configured to facilitate a second level of wireless communication between the electronic device and the implantable device a determination that the first vibration activity is the second iteration of vibration activity, and wherein the second level of wireless communication comprises receipt of information from the electronic device configured to at least one of program or change an operation of the implantable device or an associated implantable device.

15. The implantable device of claim 14, wherein the associated implantable device comprises an implantable medical device.

16. The implantable device of claim 11, wherein the electronic device comprises a mobile telephone.

17. A non-transitory computer-readable storage medium storing executable instructions that, in response to execution, cause a device comprising a processor to perform operations, comprising:
detecting first vibration activity generated by an electronic device external to an implantable device, wherein the first vibration activity comprises one or more defined vibration behaviors;
determining whether the first vibration activity has a defined correlation with a first vibration pattern identifier; and
facilitating a first level of wireless communication associated with one of a plurality of levels of wireless communication between the electronic device and the implantable device based on determining that the first vibration activity has the defined correlation with the first vibration pattern identifier, wherein the first level of wireless communication is based on the first vibration pattern identifier, and based on determining whether the first vibration activity is a first iteration of vibration activity or a second iteration of vibration activity.

18. The non-transitory computer-readable storage medium of claim 17, wherein the first iteration of vibration activity and the second iteration of vibration activity are associated with different vibration behaviors.

19. The non-transitory computer-readable storage medium of claim 17, wherein the facilitating comprises facilitating the first level of wireless communication determining that the first vibration activity is the first iteration of vibration activity, and wherein the first level of wireless communication comprises initiation of a telemetry session between the implantable device and the electronic device.

20. The non-transitory computer-readable storage medium of claim 17, wherein the operations further comprise:
facilitating a second level of wireless communication of the plurality of levels of wireless communication based on determining that the first vibration activity is the second iteration of vibration activity, and wherein the second level of wireless communication comprises receipt of information from the electronic device configured to at least one of program or change an operation of the implantable device or an associated implantable device.

21. The non-transitory computer-readable storage medium of claim 17, wherein the electronic device comprises a mobile device.

22. The non-transitory computer-readable storage medium of claim 20, wherein the associated implantable device comprises an implantable medical device.

23. A system, comprising:
an electronic device having one or more computer-readable instructions executable to generate first vibration activity of the electronic device, wherein the first vibration activity comprises one or more defined vibration behaviors; and
an implantable device, comprising:
 a detection component configured to detect the first vibration activity generated by the electronic device based on a location of the electronic device external to and within a defined proximity of the implantable device;
 an analysis component configured to determine whether the first vibration activity has a defined level of similarity with a first vibration pattern identifier; and
 a communication component configured to conduct a secure telemetry session between the implantable device and the electronic device based on a determination that the first vibration activity has the defined level of similarity with the first vibration pattern identifier, wherein the secure telemetry session facilitates a defined type of wireless communication session between the implantable device and the electronic device and wherein the defined type of wireless communication session is selected from a plurality of defined types of wireless communication sessions based on the first vibration pattern identifier.

24. The system of claim 23, wherein the electronic device comprises a mobile device.

25. The system of claim 24, wherein the mobile device comprises a mobile telephone.

26. The system of claim 23, further comprising:
a server device configured to transmit information to the electronic device, wherein the information is indicative of the one or more computer-readable instructions to generate the first vibration activity of the electronic device.

27. The system of claim 23, wherein the plurality of defined types of wireless communication sessions comprises at least one of a read only wireless communication session or a read and program wireless communication session.

28. The implantable device of claim 1, wherein the plurality of defined types of wireless communication sessions comprises at least one of a read only wireless communication session or a read and program wireless communication session.

* * * * *